United States Patent [19]
Kim et al.

[11] Patent Number: 5,559,108
[45] Date of Patent: Sep. 24, 1996

[54] CEPHALOSPORIN DERIVATIVES

[75] Inventors: Choung U. Kim, San Carlos, Calif.; Muzammil M. Mansuri, Lexington, Mass.; Peter F. Misco, Jr., Durham, Conn.; John A. Wichtowski, Deep River, Conn.; Joanne J. Bronson, Madison, Conn.; Stanley V. D'Andrea, Middletown, Conn.; Thomas W. Hudyma, Durham, Conn.

[73] Assignee: Bristol-Myers Squibb Company, Princeton, N.J.

[21] Appl. No.: 445,628

[22] Filed: May 22, 1995

Related U.S. Application Data

[63] Continuation-in-part of Ser. No. 300,830, Sep. 2, 1994, abandoned.

[51] Int. Cl.[6] .................... C07D 501/38; A61K 31/545
[52] U.S. Cl. ............... 514/203; 544/224; 544/225
[58] Field of Search .................... 540/225, 224; 514/203

[56] References Cited

U.S. PATENT DOCUMENTS 3,217,000  11/1965  Flynn ............................ 260/243
4,056,676  11/1977  Huffmann ........................ 544/29

*Primary Examiner*—John M. Ford
*Attorney, Agent, or Firm*—David M. Morse

[57] ABSTRACT

Novel cephem derivatives represented by the general formula

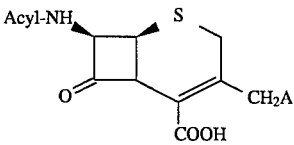

in which the Acyl substituent is a group of the formula

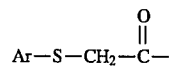

where Ar is a substituted phenyl or optionally substituted naphthyl or benzthiazolyl group and A is a substituted-pyridinium group are gram-positive antibiotics, especially useful in the treatment of diseases caused by methicillin-resistant *Staphylococcus aureus*.

13 Claims, No Drawings

CEPHALOSPORIN DERIVATIVES

CROSS-REFERENCE TO RELATED APPLICATIONS

This application is a continuation-in-part application of U.S. patent application Ser. No. 08/300,830 filed Sep. 2, 1994, now abandoned.

BACKGROUND OF THE INVENTION

1. Field of the Invention

The present invention is directed to new cephem derivatives represented by the general formula

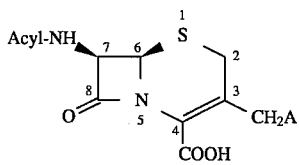

in which the Acyl substituent is a group of the formula

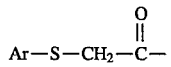

where Ar is a substituted phenyl or optionally substituted naphthyl or benzthiazolyl group and A is a substituted-pyridinium group. The derivatives are gram-positive antibiotics, especially useful in the treatment of diseases caused by methicillin-resistant *Staphylococcus aureus* (also referred to below as MRSA or methicillin-resistant *S. aureus*).

2. Description of the Prior Art

The cephalosporin class of β-lactam antibiotics is frequently employed in the treatment of diseases caused by a wide variety of bacteria because they are generally both effective and nontoxic. Several generations of cephalosporins have been developed over the years, and there are now suitable commercially available cephalosporins for most types of pathogenic bacteria.

One notable exception to the above are the so-called methicillin-resistant strains of *Staphylococcus aureus* (MRSA) which have emerged as a serious problem, particularly in hospitals and long-term care facilities.

During the late 1950's the penicillin derivative, methicillin, was introduced to treat penicillinase-resistant strains of *S. aureus*. Since that time, methicillin-resistant strains of *S. aureus* have been observed and today such strains are a major source of infectious disease in hospital settings. Such hospital-acquired (i.e. nosocomial) infections, especially in burn units and intensive care wards, frequently cause life-threatening disease, including pneumonia, bacteremia and endocarditis. The number of effective therapeutic agents against MRSA is extremely limited.

The β-lactam antibiotics, including those of the cephalosporin class, have been notably ineffective against MRSA.

At the present time, intravenous vancomycin is the antibiotic of choice for the treatment of infections caused by such bacteria. The occasional failure of patients with severe MRSA infection to respond to vancomycin therapy, the belief that significant clinical resistance to vancomycin will eventually develop, and the side effects associated with vancomycin, e.g. ototoxicity and nephrotoxicity, have led to a search for alternative antibiotics to vancomycin therapy. One object of the present invention is to provide cephalosporin derivatives which are effective against MRSA infections and yet have a better side-effect profile than vancomycin.

The literature discloses a vast number of cephem derivatives having a wide variety of C-3 and C-7 substituents. Among the references directed to compounds having 3-pyridiniummethyl substituents and 7-substituents of the type

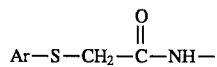

where Ar is an aromatic group are the following:

U.K. Patent 1,350,238 discloses the cephems of the formula

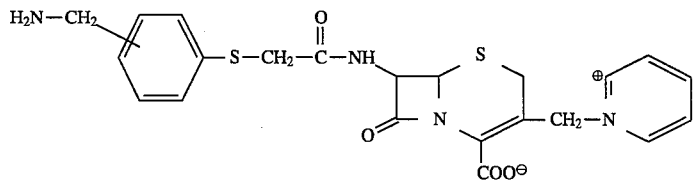

wherein the aminomethyl substituent may be at the ortho-, meta- or para- position of the phenyl group as being useful in the treatment of infectious diseases caused by gram-positive and gram-negative bacteria.

U.S. Pat. No. 4,056,676 discloses cephem derivatives of the general formula

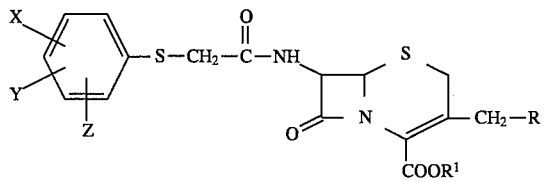

where Z is hydrogen or fluorine; and when Z is hydrogen, each of X and Y is hydrogen or chlorine selected so that the phenyl ring is substituted with 1 or 2 chlorine atoms and so that when one chlorine atom is present said chlorine atom is in the 3-position, and when two chlorine atoms are present said chlorine atoms are in the 3,4-, the 3,5- or the 2,5- positions; and when Z is fluorine, said fluorine is in the 3- or 4-positions of the phenyl ring and each of X and Y is hydrogen or chlorine selected so that when the phenyl ring is substituted with 1 or 2 chlorine atoms, one of the chlorine atoms is in the 3- or 4-position of the phenyl ring; $R^1$ is hydrogen, dicyclohexylamine, or a pharmaceutically acceptable cation; and R is, inter alia, N-pyridino. Among the compounds specifically disclosed are those of the formulae:

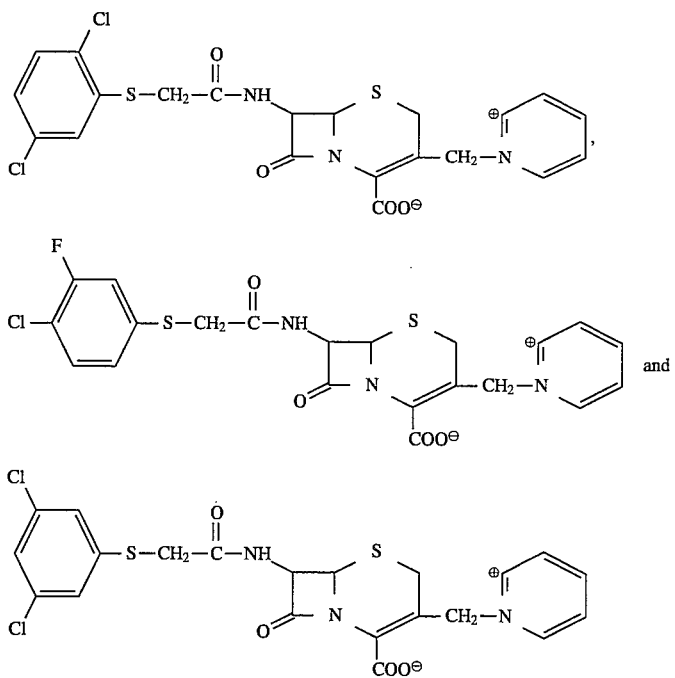

The compounds disclosed are said to be useful for treating and inhibiting the growth of MRSA organisms.

The cephalosporin derivative of the formula

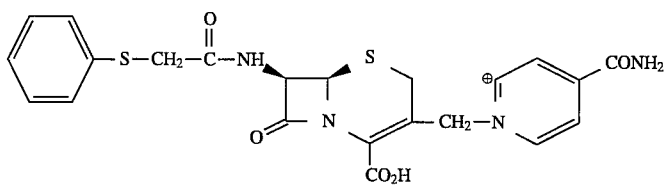

is disclosed in *Antimicrobial Agents and Chemotherapy*—1966, pg. 573–580 at page 576 (Compound No. 48).

*J. Antibiotics*, 26(12), 737–744, 1973, discloses the compound of the formula

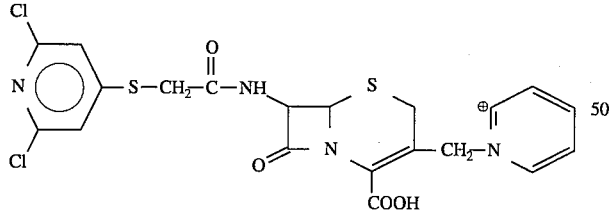

U.K. Patent 998,265 discloses cephem derivatives of the general formula

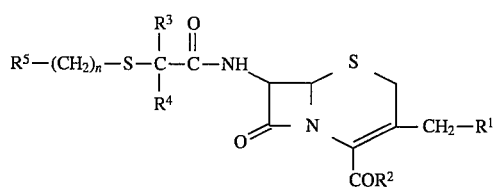

in which $R^1$, taken alone, is —OH, $C_1$–$C_8$ acyloxy, or tertiaryamino, $R^2$ is —OH when $R^1$ is —OH, $R^2$ is —OH when $R^1$ is $C_1$–$C_8$ acyloxy, $R^2$ is —O— when $R^1$ is tertiaryamino, $R^1$ and $R^2$, when taken together, are —O—, $R^3$ and $R^4$ represent hydrogen, alkyl radicals having from 1 to 6 carbon atoms, alkenyl radicals having from 2 to 6 carbon atoms, cycloalkyl radicals having from 5 to 7 carbon atoms, or alkoxyalkyl radicals having from 2 to 6 carbon atoms; n represents 0 to 4; and $R^5$ represents an alkyl radical having from 1 to 6 carbon atoms, an alkenyl or alkynyl radical having from 2 to 6 carbon atoms, a cycloalkyl radical having 5 or 6 carbon atoms, phenyl, β-furyl, β-thienyl, thienyl, or naphthyl, or a fluoro, chloro, bromo, nitro, trifluoromethyl, $C_1$–$C_4$ alkyl, $C_1$–$C_4$ alkylmercapto, or $C_1$–$C_4$ alkoxy substitution product of such radicals.

U.K. Published Application No. 2,007,221 A discloses cephalosporin derivatives of the formula

5

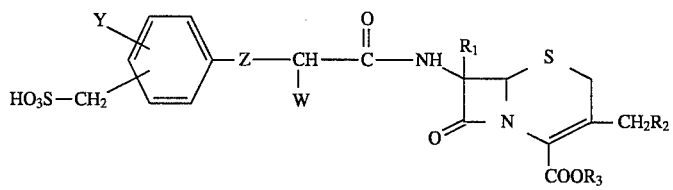

wherein Y is hydrogen, chlorine, bromine, $C_1$–$C_4$ alkyl or $C_1$–$C_4$ alkoxy; Z is a bond, oxygen or sulfur; W is hydrogen, methyl, amino, hydroxy, $SO_3H$ or $COOR_4$ wherein $R_4$ is hydrogen or 5-indanyl with the proviso that when Z is oxygen or sulfur, W is other than hydroxy; $R_1$ is hydrogen or methoxy; $R_2$ is hydrogen, acetoxy, 1,3,4-thiadiazol-2-ylthio, 5-methyl-1,3,4-thiadiazol-2-ylthio, tetrazol- 5-ylthio, 1-methyltetrazol-5-ylthio, 1,3,4-oxadiazol-2-ylthio, 5-methyl- 1,3,4-oxadiazol-2-ylthio, 1,3,4-triazol-2-ylthio, 5-methyl-1,3,4-triazol-2-ylthio, 1,2,3-triazol-5-ylthio, pyridinium or 4-aminocarbonylpyridinium; $R_3$ is hydrogen, a negative charge when $R_2$ is pyridinium or 4-aminocarbonylpyridinium, a cation of an alkali metal or an alkaline earth metal, ammonium or organic ammonium cations, $C_1$–$C_4$ alkyl, ($C_{2-5}$alkanoyloxy)methyl, ($C_{2-5}$alkanoylamino)methyl, [$C_{2-5}$alkanoyl($C_{1-4}$alkyl)amino]methyl, ($C_{1-4}$alkoxy)-carbonylaminomethyl, ($C_{1-4}$alkoxy)carbonyl($C_{1-4}$alkyl)-amino-methyl, p-($C_2$-alkanoyloxy)benzylamino($C_{2-15}$alkanoyloxy)methyl, ($C_{1-4}$alkyl)amino($C_{2-15}$alkanoyloxy)methyl or di($C_{1-4}$alkyl)amino($C_{2-15}$alkanoyloxy)methyl; and pharmaceutically acceptable salts thereof.

U.K. Patent 1,073,996 discloses cephem derivatives of the formula

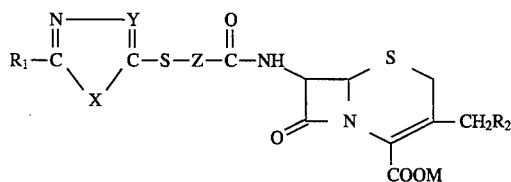

wherein $R_1$ is a lower alkyl, lower alkanoylamino, pyridyl, aryl, halo, and/or nitro substituted aryl radical; $R_2$ is an acetoxy, pyridinium, amino-pyridinium, imidazolium or methyl-imidazolium group; X is an oxygen or sulfur atom; Y is a nitrogen atom or the group =CH—; Z is the group —$CH_2$— or —$CH_2$—$CH_2$—; and M is a hydrogen atom, a pharmaceutically acceptable non-toxic cation or an anionic charge.

U.S. Pat. No. 3,217,000 discloses cephem derivatives of the formula

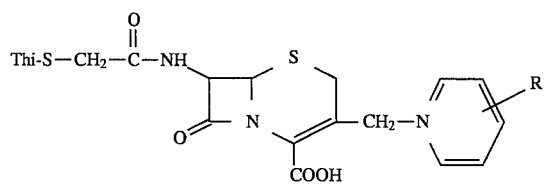

wherein Thi is 2-thienyl or 3-thienyl and R is a substituent at the 3 or 4 position of the pyridino ring selected from the group consisting of cyano, carboxy, carbamyl, N-methylcarbamyl, carbo ($C_1$–$C_4$ alkoxy), hydroxy and ($C_1$–$C_4$)alkanoyl; and the salts thereof with pharmaceutically acceptable acids.

6

SUMMARY OF THE INVENTION

The present invention provides a novel series of cephem derivatives of the general formula

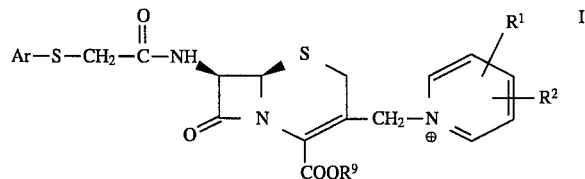

wherein Ar is an aryl group selected from the group consisting of

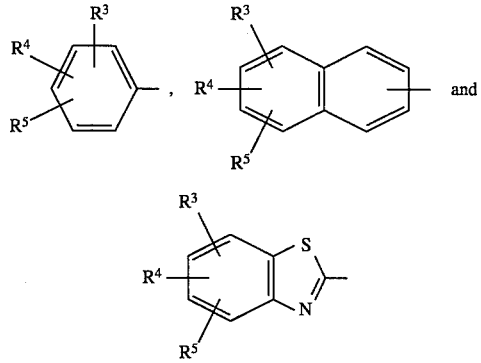

in which $R^3$, $R^4$ and $R^5$ are each independently hydrogen, halogen, trihalomethyl, $C_1$–$C_6$ alkyl, —$(CH_2)_n$ $OR^6$ or —$(CH_2)_n SR^6$, with the proviso that when Ar is a phenyl group, $R^3$, $R^4$ and $R^5$ may not all be hydrogen; n is an integer of from 1 to 6; $R^6$ is hydrogen or $C_1$–$C_6$ alkyl; $R^1$ and $R^2$ are each independently hydrogen, —$(CH_2)_m CONR^7R^8$, —$(CH_2)_m COR^7$, —$(CH_2)_m CO_2 R^7$, —$(CH_2)_m CN$, —$(CH^2)_m NR^7R^8$, —$(CH_2)_m OR^7$, —$(CH_2)_m NHCONR^7R^8$ or —$(CH_2)_m NHCOR^7$ in which m is 0 or an integer of from 1 to 6 and $R^7$ and $R^8$ are each independently hydrogen, $C_1$–$C_6$ alkyl substituted by one or two amino or hydroxyl groups or a group of the formula

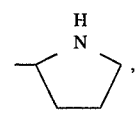

or $R^7$ and $R^8$ taken together with the nitrogen atom to which they are attached represent

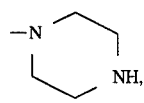

with the proviso that $R^1$ and $R^2$ may not both be hydrogen; and $R^9$ is hydrogen, an anionic charge or a carboxyl-protecting group, provided that when $R^9$ is hydrogen or a protecting group, there is also present a counter ion; or a pharmaceutically acceptable salt thereof. The compounds of formula I are antibacterial agents useful in the treatment of infections in humans and other animals caused by a variety of gram-positive bacteria, particularly methicillin-resistant *S. aureus*.

Also included in the invention are processes for preparing the compounds of formula I and pharmaceutical compositions containing said compounds in combination with pharmaceutically acceptable carriers or diluents.

DETAILED DESCRIPTION

The present invention provides novel cephem derivatives of general formula I above which are antibacterial agents useful in the treatment of infectious diseases in humans and other animals. The compounds exhibit good activity against a variety of gram-positive microorganisms, e.g. *S. pneumoniae, S. pyogenes, S. aureus, E. faecalis, E. faecium, S. epidermidis* and *S. hemolyticus*, and are particularly useful against strains of methicillin-resistant *S. aureus*.

The compounds of formula I are characterized by a substituted-pyridiniummethyl group at the 3-position of the cephem ring and a lipophilic 7-substituent of the formula

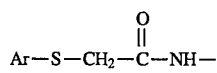

wherein Ar is an aromatic group selected from substituted phenyl or optionally substituted naphthyl or benzthiazolyl.

To elaborate on the definitions for the substituents of the formula I compounds:

(a) "Halogen" includes chloro, bromo, fluoro and iodo, and is preferably chloro or bromo;

(b) "Trihalomethyl" includes trichloromethyl, trifluoromethyl, tribromomethyl and triiodomethyl, but is preferably trifluoromethyl;

(c) The term "$C_1$–$C_6$ alkyl" means straight and branched chain alkyl groups having from 1–6 carbon atoms such as methyl, ethyl, propyl, isopropyl, butyl, isobutyl, t-butyl, amyl, hexyl, and the like. Preferably these groups contain from 1–4 carbon atoms and, most preferably, they contain 1 or 2 carbon atoms.

The term "pharmaceutically acceptable salt" as used herein is intended to include the nontoxic acid addition salts with inorganic or organic acids, e.g. salts with acids such as hydrochloric, phosphoric, sulfuric, maleic, acetic, citric, succinic, benzoic, fumaric, mandelic, p-toluenesulfonic, methanesulfonic, ascorbic, lactic, gluconic, trifluoroacetic, hydroiodic, hydrobromic, and the like. Some of the compounds of the present invention have an acidic hydrogen and can, therefore, be converted with bases in a conventional manner into pharmaceutically acceptable salts. Such salts, e.g. ammonium, alkali metal salts, particularly sodium or potassium, alkaline earth metal salts, particularly calcium or magnesium, and salts with suitable organic bases such as lower alkylamines (methylamine, ethylamine, cyclohexylamine, and the like) or with substituted lower alkylamines (e.g. hydroxyl-substituted alkylamines such as diethanolamine, triethanolamine or tris- (hydroxymethyl) aminomethane), or with bases such as piperidine or morpholine, are also intended to be encompassed by the term "pharmaceutically acceptable salt".

Compounds of formula I in the form of acid addition salts may be written as

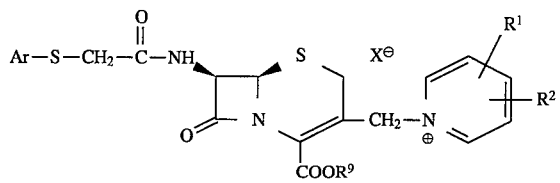

where $X^\ominus$ represents the acid anion and $R^9$ is hydrogen or a carboxyl-protecting group. The counter anion $X^\ominus$ may be selected so as to provide pharmaceutically acceptable salts for therapeutic administration.

The carboxyl-protecting group $R^9$ is intended to include readily removable ester groups which have been employed to block a carboxyl group during the reaction steps used to prepare compounds I and which can be removed by methods which do not result in any appreciable destruction of the remaining portion of the molecule, e.g. by chemical or enzymatic hydrolysis, treatment with chemical reducing agents under mild conditions, irradiation with ultraviolet light or catalytic hydrogenation. Examples of such protecting groups include benzhydryl, p-nitrobenzyl, 2-naphthylmethyl, allyl, benzyl, trichloroethyl, silyl such as trimethylsilyl, phenacyl, acetonyl, o-nitrobenzyl, 4-pyridylmethyl and $C_1$–$C_6$ alkyl such as methyl, ethyl or t-butyl. Included within such protecting groups are those which are hydrolyzed under physiological conditions such as pivaloyloxymethyl, acetoxymethyl, phthalidyl, indanyl, α-acetoxyethyl, α-acetoxybenzyl, p-methoxybenzyl, α-pivaloyloxyethyl, and methoxymethyl. Compounds of formula I wherein $R^9$ is a physiologically removable protecting group are useful directly as antibacterial agents. Compounds where $R^9$ is not physiologically removable are useful intermediates which can be easily converted to the active form by conventional deblocking procedures well-known to those skilled in the art.

A preferred embodiment of the present invention comprises compounds of formula I wherein Ar is

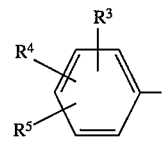

in which $R^3$, $R^4$ and $R^5$ are each independently hydrogen, halogen, trihalomethyl, $C_1$–$C_6$ alkyl, —$(CH_2)_n$ $OR^6$ or —$(CH_2)_nSR^6$, with the proviso that $R^3$, $R^4$ and $R^5$ may not all be hydrogen; n is an integer of from 1 to 6; and $R^6$ is hydrogen or $C_1$–$C_6$ alkyl. Among this subgroup, the preferred compounds are those wherein $R^3$, $R^4$ and $R^5$ are each independently hydrogen, halogen, trihalomethyl or $C_1$–$C_6$ alkyl and the most preferred of these are those where $R^2$ is hydrogen and $R^1$ is —$(CH_2)_mCONR^7R^8$, —$(CH_2)_m$ $COR^7$, —$(CH_2)_mCN$, —$(CH_2)_mNR$ $^7R^8$, —$(CH_2)_mOR^7$, —$(CH^2)_mNHCONR$ $^7R^8$ or $(CH_2)_mNHCOR^7$ in which $R^7$ and $R^8$ are each independently hydrogen, $C_1$–$C_6$ alkyl substituted by one or two amino or hydroxyl groups or a group of the formula

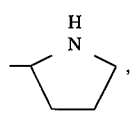

or $R^7$ and $R^8$ taken together with the nitrogen atom to which they are attached represent

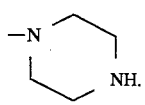
A most preferred embodiment of the present invention comprises a subgroup of the compounds of formula I having the formula
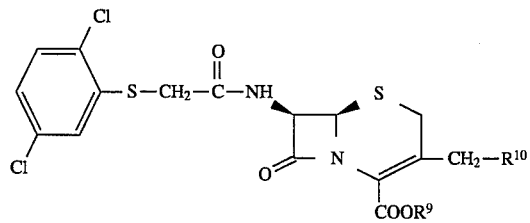 (a)
wherein $R^{10}$ is
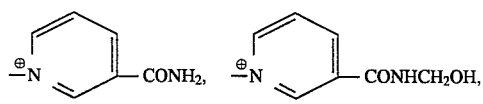
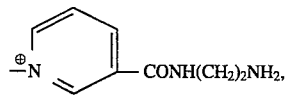
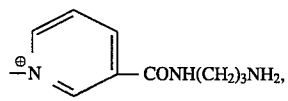
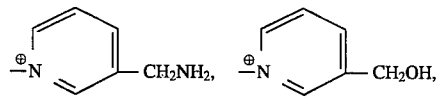
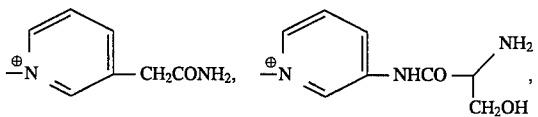
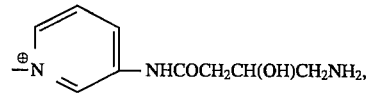
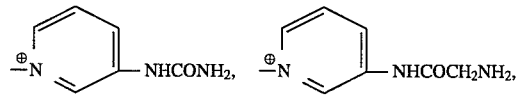
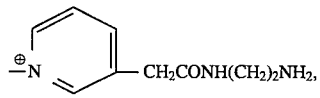
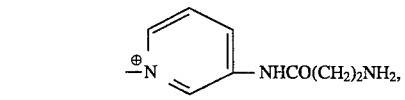
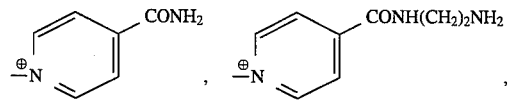
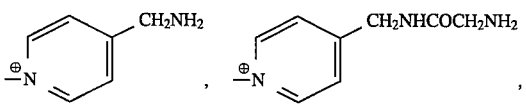
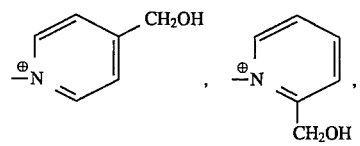
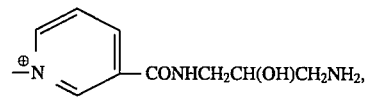
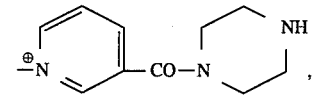
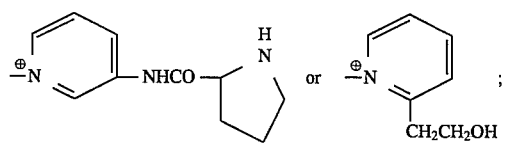
and $R^9$ is hydrogen, an anionic charge or a carboxyl-protecting group, provided that when $R^9$ is hydrogen or an ester group, there is also present a counter ion;
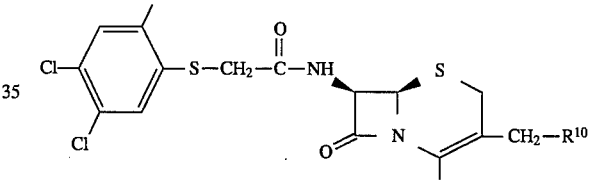 (b)
wherein R 10 is
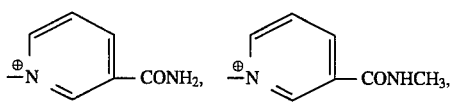
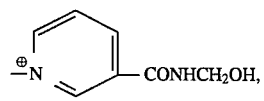
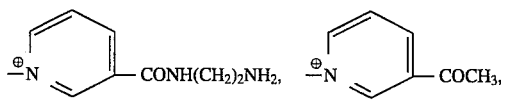
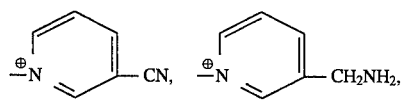
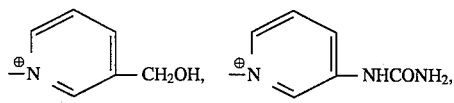
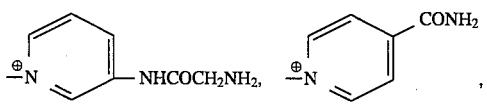

and R⁹ is as defined above;
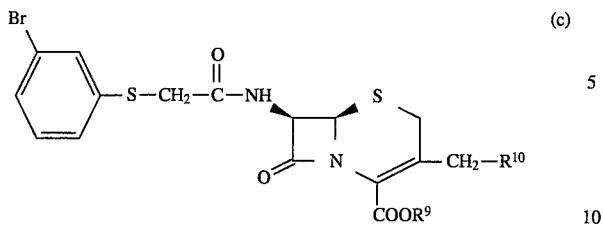
(c)
wherein R¹⁰ is
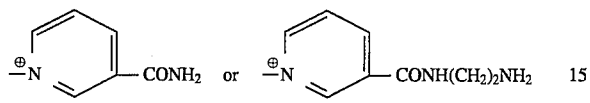
and R⁹ is as defined above;
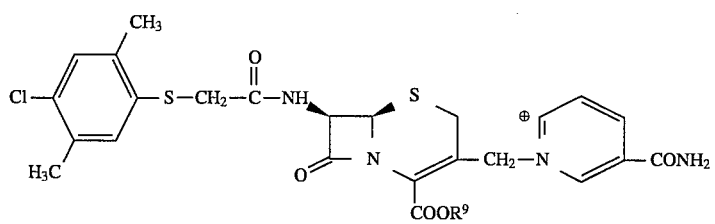
(d)
wherein R⁹ is as defined above;
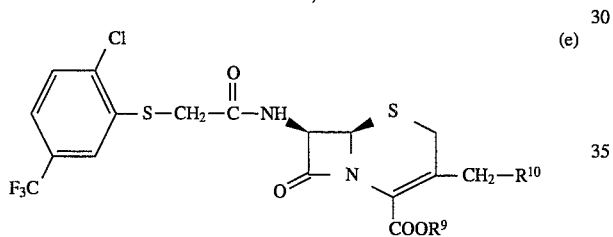
(e)
wherein R¹⁰ is
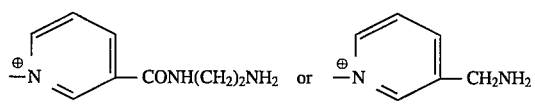
and R⁹ is as defined above;
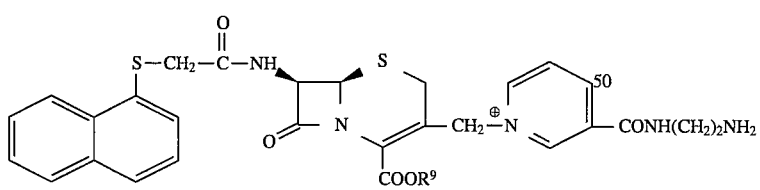
(f)

and $R^9$ is as defined above; or

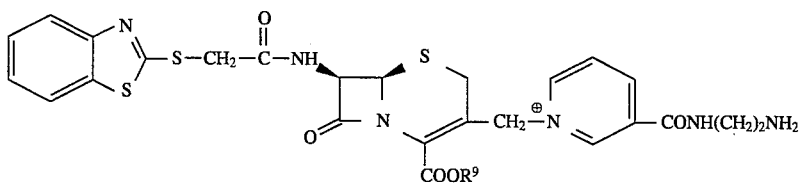

and $R^9$ is as defined above; or a pharmaceutically acceptable salt thereof.

These most preferred compounds mentioned just above have unexpectedly been found to have both excellent in vitro activity against a representative MRSA strain (MIC≦8 μg/ml) and excellent in vivo activity against such strain, as measured by the standard mouse system MRSA infection model ($PD_{50}$, which is the dose in mg/kg required to give protection to 50% of the infected mice, ≦5). Applicants have found that only a small group of cephem derivatives possess this desirable profile of activity against MRSA.

The preferred individual compounds of the present invention are listed below:

1-[[(6R)-trans-2-Carboxy-8-oxo- 7-[2-(2,5-dichlorophenylthio)acetamido]- 5-thia-1-azabicyclo[4.2.0]-oct-2-en- 3-yl]methyl]-3-(aminocarbonyl)pyridinium inner salt (Example 3 below)

1-[[(6R)-trans-2-Carboxy-8-oxo- 7-[2-(2,4,5-trichlorophenylthio)acetamido]- 5-thia-1-azabicyclo[4.2.0]-oct-2-en- 3-yl]methyl]-3-(aminocarbonyl)pyridinium inner salt (Example 1 below)

1-[[(6R)-trans-2-Carboxy-8-oxo- 7-[2-(3-bromophenylthio)acetamido]-thia- 1-azabicyclo[4.2.0]-oct-2-en-3-yl]methyl]-3-(aminocarbonyl)pyridinium inner salt (Example 4 below)

1-[[(6R)-trans-2-Carboxy-8-oxo- 7-[2-(2,5-dimethyl-4-chlorophenylthio)acetamido ]-5-thia-1-azabicyclo [4.2.0]-oct-2-en- 3-yl]methyl]-3-(aminocarbonyl)pyridinium inner salt (Example 5 below)

1-[[(6R)-trans-2-Carboxy-8-oxo- 7-[2-(2,4,5-trichlorophenylthio)acetamido]-5-thia-1-azabicyclo[4.2.0]-oct-2-en- 3-yl]methyl]-3-(methylaminocarbonyl)-pyridinium inner salt (Example 6 below)

1-[[(6R)-trans-2-Carboxy-8-oxo- 7-[2-(2,5-dichlorophenylthio)acetamido]- 5-thia-1-azabicyclo[4.2.0]-oct-2-en- 3-yl]methyl]-3-[(hydroxymethyl)aminocarbonyl]-pyridinium inner salt (Example 7 below)

1-[[(6R)-trans-2-Carboxy-8-oxo- 7-[2-(2,4,5-trichlorophenylthio)acetamido]-5-thia-1-azabicyclo[4.2.0]-oct-2-en- 3yl]methyl]-3-[(hydroxymethyl)aminocarbonyl]-pyridinium inner salt (Example 8 below)

1-[[(6R)-trans-2-Carboxy-8-oxo- 7-[2-(2,5-dichlorophenylthio )acetamido]-5-thia-1-azabicyclo[4.2.0]-oct-2-en- 3-yl]methyl]-3-[(2-aminoethyl)aminocarbonyl]-pyridinium inner salt (Example 9 below)

1-[[(6R)-trans-2-Carboxy-8-oxo- 7-[2-(2,4,5-trichlorophenylthio)acetamido]-5-thia-1-azabicyclo[4.2.0]-oct-2-en- 3yl]methyl]-3-[(2-aminoethyl)aminocarbonyl]-pyridinium inner salt (Example 10 below)

1-[[(6R)-trans-2-Carboxy-8-oxo- 7-[2-(3-bromophenylthio)acetamido]-5-thia- 1-azabicyclo[4.2.0]-oct-2-en-3-yl]methyl]-3-[(2-aminoethyl)aminocarbonyl]-pyridinium inner salt (Example 11 below)

1-[[(6R)-trans-2-Carboxy-8-oxo- 7-[2-(2-chloro- 5-trifluoromethylphenylthio)-acetamido]-5-thia- 1-azabicyclo[4.2.0]-oct-2-en-3-yl]methyl]-3-[(2-aminoethyl)aminocarbonyl]pyridinium inner salt (Example 12 below)

1-[[(6R)-trans-2-Carboxy-8-oxo- 7-[2-(1-naphthylthio)acetamido]-5-thia-1 -azabicyclo[4.2.0]-oct-2-en-3-yl] methyl]- 3-[(2-aminoethyl)aminocarbonyl]-pyridinium inner salt (Example 13 below)

1-[[(6R)-trans-2-Carboxy-8-oxo- 7-[2-(2-benzthiazolylthio)acetamido]-5-thia- 1-azabicyclo[4.2.0]-oct-2-en-3-yl]methyl]-3-[(2-aminoethyl)aminocarbonyl]-pyridinium inner salt (Example 14 below)

1-[[(6R)-trans-2-Carboxy-8-oxo- 7-[2-(2,5-dichlorophenylthio)acetamido]-5 -thia-1-azabicyclo[4.2.0]-oct-2-en- 3-yl]methyl]-3-[(3-aminopropyl)aminocarbonyl] pyridinium inner salt (Example 15 below)

1-[[(6R)-trans-2-Carboxy-8-oxo- 7-[2-(2,4,5-trichlorophenylthio)acetamido]- 5-thia-1-azabicyclo[4.2.0]-oct-2-en- 3-yl]methyl]-3-(acetyl)pyridinium inner salt (Example 16 below)

1-[[(6R)-trans-2-Carboxy-8-oxo- 7-[2-(2,4,5-trichlorophenylthio)acetamido]- 5-thia-1-azabicyclo[4.2.0]-oct-2-en-3 -yl]methyl]-3-(cyano)pyridinium inner salt (Example 17 below)

1-[[(6R)-trans-2-Carboxy-8-oxo- 7-[2-(2,5-dichlorophenyl-thio)acetamido]- 5-thia-1-azabicyclo[4.2.0]-oct-2-en- 3-yl]methyl]-3-(aminomethyl)pyridinium inner salt (Example 18 below)

1-[[(6R)-trans-2-Carboxy-8-oxo- 7-[2-(2,4,5-trichlorophenylthio)acetamido]- 5-thia-1-azabicyclo[4.2.0]-oct-2-en-3 -yl]methyl]-3-(aminomethyl)pyridinium inner salt (Example 19 below)

1-[[(6R)-trans-2-Carboxy-8-oxo- 7-[2-(2-chloro- 5-trifluoromethylphenylthio)-acetamido]-5-thia- 1-azabicyclo[4.2.0]-oct-2-en-3-yl]methyl]-3-(aminomethyl)pyridinium inner salt (Example 20 below)

1-[[(6R)-trans-2-Carboxy-8-oxo- 7-[2-(2,5-dichlorophenylthio)acetamido]-5 -thia-1-azabicyclo[4.2.0]-oct-2-en-3-yl]methyl]-3-(hydroxymethyl)pyridinium inner salt (Example 21 below)

1-[[(6R)-trans-2-Carboxy-8-oxo- 7-[2-(2,4,5-trichlorophenylthio)acetamido]- 5-thia-1-azabicyclo[4.2.0]-oct-2-en-3 -yl]methyl]-3-(hydroxymethyl)pyridinium inner salt (Example 22 below)

1-[[(6R)-trans-2-Carboxy-8-oxo- 7-[2-(2,5-dichlorophenylthio)acetamido]- 5-thia-1-azabicyclo[4.2.0]-oct-2-en- 3-yl]methyl]-3-(carbamylmethyl)pyridinium inner salt (Example 23 below)

1-[[(6R)-trans-2-Carboxy-8-oxo-7 -[2-(2,5-dichlorophenylthio)acetamido]- 5-thia-1-azabicyclo[4.2.0]-oct-2-en- 3-yl]methyl]-3-(ureido)pyridinium inner salt (Example 24 below)

1-[[(6R)-trans-2-Carboxy-8-oxo- 7-[2-(2,4,5-trichlorophenylthio)acetamido]- 5-thia-1-azabicyclo[4.2.0]-oct-2-en-3 -yl]methyl]-3-(ureido)pyridinium inner salt (Example 25 below)

1-[[(6R)-trans-2-Carboxy-8-oxo- 7-[2-(2,5-dichlorophenylthio)acetamido]- 5-thia-1-azabicyclo[4.2.0]-oct-2- en- 3-yl]methyl]-3-(aminomethylcarbonylamino)pyridinium inner salt (Example 26 below)

1-[[(6R)-trans-2-Carboxy-8-oxo- 7-[2-(2,4,5-trichlorophenylthio)acetamido]- 5-thia-1-azabicyclo[4.2.0]-oct-2-en- 3-yl]methyl]-3-(aminomethylcarbonylamino)pyridinium inner salt (Example 2 below)

1-[[(6R)-trans-2-Carboxy-8-oxo- 7-[2-(2,5-dichlorophenylthio)acetamido]-5 -thia-1-azabicyclo[4.2.0]-oct-2-en-3-yl]methyl]-3-[(2-aminoethyl)carbonylamino)pyridinium inner salt (Example 27 below)

1-[[(6R)-trans-2-Carboxy-8-oxo- 7-[2-(2,5-dichlorophenylthio)acetamido]- 5-thia-1-azabicyclo[4.2.0]-oct-2-en- 3-yl]methyl]-4(aminocarbonyl)pyridinium inner salt (Example 28 below)

1-[[(6R)-trans-2-Carboxy-8-oxo- 7-[2-(2,4,5-trichlorophenylthio)acetamido]- 5-thia-1- azabicyclo[4.2.0]-oct-2-en- 3-yl]methyl]-4-(aminocarbonyl)pyridinium inner salt (Example 29 below)

1-[[(6R)-trans-2-Carboxy-8-oxo- 7-[2-(2,5-dichlorophenylthio)acetamido]- 5-thia-1-azabicyclo[4.2.0]-oct-2-en- 3-yl]methyl]-4-[(2-aminoethyl)aminocarbonyl]pyridinium inner salt (Example 30 below)

1-[[(6R)-trans-2-Carboxy-8-oxo- 7-[2-(2,4,5-trichlorophenylthio)acetamido]- 5-thia-1-azabicyclo[4.2.0]-oct-2-en- 3-yl]methyl]-4-[(2-aminoethyl)aminocarbonyl]pyridinium inner salt (Example 31 below)

1-[[(6R)-trans-2-Carboxy-8-oxo- 7-[2-(2,5-dichlorophenylthio)acetamido]-5 -thia-1-azabicyclo[4.2.0]-oct-2-en-3-yl]methyl]-4-(aminomethyl)pyridinium inner salt (Example 32 below)

1-[[(6R)-trans-2-Carboxy-8-oxo- 7-[2-(2,5-dichlorophenylthio)acetamido]- 5-thia-1-azabicyclo[4.2.0]-oct-2-en- 3-yl]methyl]-4(hydroxymethyl)pyridinium inner salt (Example 33 below)

1-[[(6R)-trans-2-Carboxy-8-oxo- 7-[2-(2,4,5-trichlorophenylthio)acetamido]- 5-thia-1-azabicyclo[4.2.0]-oct-2-en- 3-yl]methyl]-2-(aminomethyl)pyridinium inner salt (Example 34 below)

1-[[(6R)-trans-2-Carboxy-8-oxo- 7-[2-(2,5-dichlorophenylthio)acetamido]- 5-thia-1-azabicyclo[4.2.0]-oct-2-en- 3-yl]methyl]-2-(hydroxymethyl)pyridinium inner salt (Example 35 below)

1-[[(6R)-trans-2-Carboxy-8-oxo- 7-[2-(2,4,5-trichlorophenylthio)acetamido]- 5-thia-1-azabicyclo[4.2.0]-oct-2-en- 3-yl]methyl]-2-(2-aminoethyl)pyridinium inner salt (Example 36 below)

1-[[(6R)-trans-2-Carboxy-8-oxo- 7-[2-(2,5-dichlorophenylthio)acetamido]- 5-thia-1-azabicyclo[4.2.0]-oct-2-en- 3-yl]methyl]-2-(hydroxyethyl)pyridinium inner salt (Example 37 below), 1-[[(6R)-trans-2-Carboxy-8-oxo- 7-[2-(2,5-dichlorophenylthio)acetamido]- 5-thia-1-azabicyclo[4.2.0]-oct-2-en- 3-yl]methyl]-3-[(3-amino- 2-hydroxypropyl)aminocarbonyl]pyridinium inner salt (Example 38 below), 1-[[(6R)-trans-2-Carboxy-8-oxo- 7-[2-(2,5-dichlorophenylthio)acetamido]- 5-thia-1-azabicyclo[4.2.0]-oct-2-en- 3-yl]methyl]-3-(piperizino-N-carbonyl)pyridinium inner salt (Example 39 below), 1-[[(6R)-trans-2-Carboxy-8-oxo- 7-[2-(2,5-dichlorophenylthio)acetamido]- 5-thia-1-azabicyclo[4.2.0]-oct-2-en- 3-yl]methyl]-3-[(2-aminoethyl)ureido]pyridinium inner salt (Example 40 below), 1-[[(6R)-trans-2-Carboxy-8-oxo- 7-[2-(2,5-dichlorophenylthio)acetamido]- 5-thia-1-azabicyclo[4.2.0]-oct-2-en- 3-yl]methyl]-3-[(2-pyrrolidinyl)carbonylamino)pyridinium inner salt (Example 41 below), 1-[[(6R)-trans-2-Carboxy-8-oxo- 7-[2-(2,5-dichlorophenylthio)acetamido]- 5-thia-1-azabicyclo[4.2.0]-oct-2-en- 3-yl]methyl]-3-[(1-(1-amino- 2-hydroxy)ethyl)carbonylamino)pyridinium inner salt (Example 42 below), 1-[[(6R)-trans-2-Carboxy-8-oxo- 7-[2-(2,5-dichlorophenylthio)acetamido]- 5-thia-1-azabicyclo[4.2.0]-oct-2-en- 3-yl]methyl]-3-[(2-aminoethyl)carbamylmethyl]pyridinium inner salt (Example 43 below), 1-[[(6R)-trans-2-Carboxy-8-oxo- 7-[2-(2,5-dichlorophenylthio)acetamido]- 5-thia-1-azabicyclo[4.2.0]-oct-2-en- 3-yl]methyl]-4-[(aminomethylcarbonyl)aminomethyl]pyridinium inner salt (Example 44 below); and 1-[[(6R)-trans-2-Carboxy-8-oxo- 7-[2-(2,5-dichlorophenylthio)acetamido]- 5-thia-1-azabicyclo[4.2.0]-oct-2-en- 3-yl]methyl]-3-[(3-amino-2-hydroxypropyl) carbonylamino]pyridinium inner salt (Example 45 below), including the physiologically hydrolyzable esters and/or pharmaceutically acceptable salts thereof.

The more preferred individual compounds of the present invention are listed below:

1-[[(6R)-trans-2-Carboxy-8-oxo- 7-[2-(2,5-dichlorophenylthio)acetamido]- 5-thia-1-azabicyclo[4.2.0]-oct-2-en- 3-yl]methyl]-3-[(2-aminoethyl)aminocarbonyl]pyridinium inner salt (Example 9 below)

1-[[(6R)-trans-2-Carboxy-8-oxo- 7-[2-(2,4,5-trichlorophenylthio)acetamido]- 5-thia-1-azabicyclo[4.2.0]-oct-2-en- 3-yl]methyl]-3-[(2-aminoethyl)amino-carbonyl]pyridinium inner salt (Example 10 below)

1-[[(6R)-trans-2-Carboxy-8-oxo- 7-[2-(3-bromophenylthio)acetamido]-5-thia- 1-azabicyclo[4.2.0]-oct-2-en-3-yl]methyl]-3-[(2-aminoethyl)aminocarbonyl]-pyridinium inner salt (Example 11 below)

1-[[(6R)-trans-2-Carboxy-8-oxo- 7-[2-(2-chloro-5-trifluoromethylphenylthio) -acetamido]-5-thia-1-azabicyclo[4.2.0]-oct- 2-en-3-yl]methyl- 3-[(2-aminoethyl)aminocarbonyl]pyridinium inner salt (Example 12 below)

1-[[(6R)-trans-2-Carboxy-8-oxo- 7-[2-(2,5-dichlorophenylthio)acetamido]- 5-thia-1-azabicyclo[4.2.0]-oct-2-en- 3-yl]methyl]-3-[(3-aminopropyl)aminocarbonyl] pyridinium inner salt (Example 15 below)

1-[[(6R)-trans-2-Carboxy-8-oxo- 7-[2-(2,5-dichlorophenylthio)acetamido]- 5-thia-1-azabicyclo[4.2.0]-oct-2-en- 3-yl]methyl]-3-(aminomethylcarbonylamino)pyridinium inner salt (Example 26 below)

1-[[(6R)-trans-2-Carboxy-8-oxo- 7-[2-(2,4,5-trichlorophenylthio)acetamido]- 5-thia-1-azabicyclo[4.2.0]-oct-2-en- 3-yl]methyl]-3-(aminomethylcarbonyl-amino)pyridinium inner salt (Example 2 below)

1-[[(6R)-trans-2-Carboxy-8-oxo- 7-[2-(2,5-dichlorophenylthio)acetamido]- 5-thia-1-azabicyclo[4.2.0]-oct-2-en- 3-yl]methyl]-3-[(2-aminoethyl)carbonylamino) pyridinium inner salt (Example 27 below)

1-[[(6R )-trans-2-Carboxy-8-oxo- 7-[2-(2,5-dichlorophenylthio)acetamido]- 5-thia-1-azabicyclo[4.2.0]-oct-2-en- 3-yl]methyl]-4-[(2-aminoethyl)aminocarbonyl]pyridinium inner salt (Example 30 below)

1-[[(6R)-trans-2-Carboxy-8-oxo- 7-[2-(2,4,5-trichlorophenylthio)acetamido]- 5-thia-1-azabicyclo[4.2.0]-oct-2-en- 3-yl]methyl]-4-[(2-aminoethyl)aminocarbonyl]pyridinium inner salt (Example 31 below);

and

1-[[(6R)-trans-2-Carboxy-8-oxo- 7-[2-(2,5-dichlorophenylthio)acetamido]- 5-thia-1-azabicyclo[4.2.0]-oct-2- en- 3-yl]methyl]-3-[(3-amino-2-hydroxypropyl) carbonylamino]pyridinium inner salt (Example 45 below), including the physiologically hydrolyzable esters and/or pharmaceutically acceptable salts thereof.

The most preferred individual compounds of the present invention are listed below:

1-[[(6R)-trans-2-Carboxy-8-oxo- 7-[2-(2,4,5-trichlorophenylthio)acetamido]- 5-thia-1-azabicyclo[4.2.0]-oct-2-en- 3-yl]methyl]-3-[(2-aminoethyl)aminocarbonyl]pyridinium inner salt (Example 10 below);

and

1-[[(6R)-trans-2-Carboxy-8-oxo- 7-[2-(2,5-dichlorophenylthio)acetamido]- 5-thia-1-azabicyclo[4.2.0]-oct-2-en- 3-yl]methyl]-3-(aminomethylcarbonylamino)pyridinium inner salt (Example 26 below), including the physiologically hydrolyzable esters and/or pharmaceutically acceptable salts thereof.

The compounds of the present invention can be made by conventional methods. One suitable procedure is summarized by the following reaction scheme:

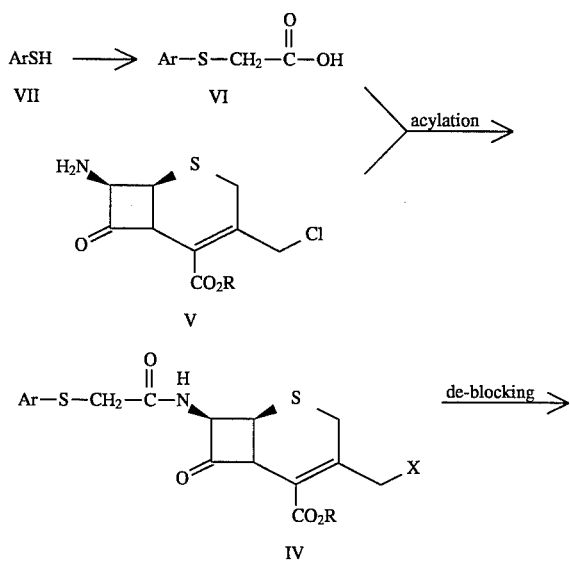

R = conventional carboxyl protecting group
such as diphenylmethyl (DPM) or
p-methoxybenzyl (PMB)

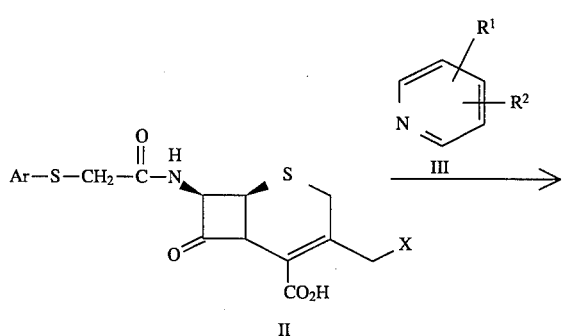

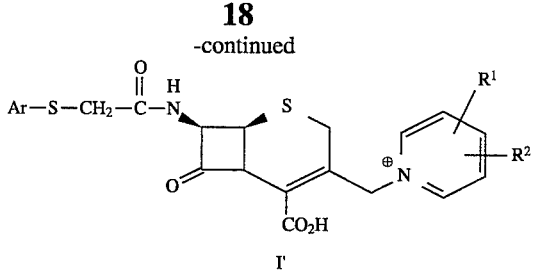

I'

To elaborate on the above process, thiol VII is converted into the arylthioacetic acid derivative VI, e.g. by treatment with bromoacetic acid under basic conditions (e.g. aqueous sodium or potassium hydroxide). The reaction temperature for this step is typically between 20° C. and 100° C. Starting thiol VII is commercially available or can be prepared according to known literature methods. The product VI is typically isolated by crystallization or, if necessary, it can be purified by chromatography.

Arylthioacetic acid VI is then coupled with a suitable cephem intermediate having a 3-substituent leaving group which can be displaced by pyridine derivative III. For example, the leaving group may be acetoxy or halo. In the preferred embodiment illustrated by the reaction scheme, the cephem intermediate is the 3-chloromethyl cephem V, but other suitable cephem intermediates with equivalent leaving groups at the 3-position could also be employed. The cephem intermediate V may be acylated with VI or a reactive derivative thereof by conventional acylation procedures well-known in the cephalosporin art to give N-acylated intermediate IV. In addition to using the free acid, e.g. with a suitable condensing agent such as dicyclohexylcarbodiimide, acylating agent VI may also be employed in the form of equivalent acylating derivatives such as an acid anhydride, mixed anhydride, activated ester or acid halide. The cephem intermediate V preferably has the carboxyl group protected by a conventional carboxyl-protecting group which can be readily removed after acylation. Examples of such protecting groups are discussed above and include benzyl, 4-nitrobenzyl, 4-methoxybenzyl, benzhydryl, diphenylmethyl, allyl, and the like. Other examples of suitable protecting groups are disclosed in *Protective Groups in Organic Synthesis*, Theodora W. Greene (John Wiley & Sons, 1981), Chapter 5. In one embodiment, intermediate V may be acylated with acid VI in the presence of dicyclohexylcarbodiimide and in an inert solvent such as tetrahydrofuran or dichloromethane. The reaction temperature is typically between about −20° C. and 50° C. Upon completion of the reaction, insoluble material is removed by filtration, the filtrate is concentrated and the residue is treated with a relatively non-polar solvent such as diethyl ether or ethyl acetate resulting in precipitation of the desired product. Alternatively, acid VI may be converted to the corresponding acid chloride, for example by treatment with thionyl chloride, with or without an inert solvent such as dichloromethane, followed by coupling with cephem amine V in the presence of a base such as triethylamine or N-methylmorpholine to give intermediate IV. Cephem IV is typically isolated by evaporation of volatile solvents followed by trituration of the compound with a relatively nonpolar solvent such as diethyl ether or ethyl acetate. This intermediate may be used in the next reaction step as the X=chloride derivative, or can be converted to the X=bromide or X=iodide derivative by treatment with the appropriate metal halide in an inert solvent such as acetone.

Intermediate IV may then be deprotected to remove the carboxyl protecting group, e.g. by treatment with an acid such as trifluoroacetic acid or hydrochloric acid when a diphenylmethyl or 4-methoxyphenyl protecting group is employed, to give the desired carboxylic acid intermediate II. This deprotection reaction may be carried out with or without an inert solvent such as dichloromethane. A reagent such as anisole may also be employed to scavenge the liberated ester protecting group.

The desired compounds of general formula I may be prepared by reacting a compound of the formula

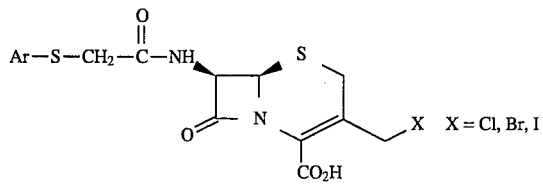

wherein Ar is as defined above with a pyridine derivative of the formula

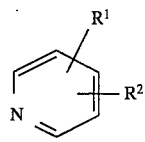

wherein $R^1$ and $R^2$ are as defined above. The reaction is carried out in the presence of an inert solvent, e.g. tetrahydrofuran, dimethylformamide or acetone, or mixtures of such solvents, at a temperature between about 0° C. and 80° C. A catalytic or stoichiometric amount of sodium iodide may be employed, if desired, in the case where X=chloride. Although the 3-halomethyl intermediate II is illustrated above, other intermediates having equivalent leaving groups could also be employed, e.g. the 3-acetoxymethyl intermediate. The desired product may be isolated by crystallization from an appropriate solvent and may be obtained either as the zwitterion or in the form of a pharmaceutically acceptable acid addition salt.

It will be understood that where the $R^1$ and/or $R^2$ groups used in the above reactions contain certain reaction-sensitive functional groups such as hydroxy or amino groups which might result in undesirable side-reactions, such groups may be protected by conventional protecting groups known to those skilled in the art. Such protecting groups are removed following the displacement reaction with the pyridine derivative III, e.g. a t-butoxycarbonyl protecting group can be removed by treatment with an acid such as trifluoroacetic acid. Suitable protecting groups and methods for their removal are known in the art and are illustrated in the reference work cited above in connection with carboxyl-protecting groups.

The desired end-product of formula I may be recovered either as the zwitterion or in the form of a pharmaceutically acceptable acid addition salt, e.g. by addition of the appropriate acid such as HCl, HI or methanesulfonic acid to the zwitterion. Compounds of formula I where $R^9$ is hydrogen or an anionic charge, or a pharmaceutically acceptable salt thereof, may be converted by conventional procedures to a corresponding compound where $R^9$ is a physiologically hydrolyzable ester group.

The novel cephalosporin derivatives of general formula I wherein $R^9$ is hydrogen, an anionic charge or a physiologically hydrolyzable carboxyl-protecting group, or the pharmaceutically acceptable salts thereof, are potent antibiotics active against many gram-positive bacteria. While they may be used, for example, as animal feed additives for promotion of growth, as preservatives for food, as bactericides in industrial applications, for example, in waterbased paint and in the white water of paper mills to inhibit the growth of harmful bacteria and as disinfectants for destroying or inhibiting the growth of harmful bacteria on medical and dental equipment, they are especially useful in the treatment of infectious disease in humans and other animals caused by the gram positive bacteria sensitive to the new derivatives. Because of their excellent activity against MRSA organisms, they are particularly useful in the treatment of infections resulting from such bacteria.

The pharmaceutically active compounds of this invention may be used alone or formulated as pharmaceutical compositions comprising, in addition to the active cephem ingredient, a pharmaceutically acceptable carrier or diluent. The compounds may be administered by a variety of means, for example, orally, topically or parenterally (intravenous or intramuscular injection). The pharmaceutical compositions may be in solid form such as capsules, tablets, powders, etc. or in liquid form such as solutions, suspensions or emulsions. Compositions for injection, the preferred route of delivery, may be prepared in unit dose form in ampules or in multidose containers and may contain additives such as suspending, stabilizing and dispersing agents. The compositions may be in ready-to-use form or in powder form for reconstitution at the time of delivery with a suitable vehicle such as sterile water.

The dosage to be administered depends, to a large extent, on the particular compound being used, the particular composition formulated, the route of administration, the nature and condition of the host and the particular situs and organism being treated. Selection of the particular preferred dosage and route of application, then, is left to the discretion of the physician or veterinarian. In general, however, the compounds may be administered parenterally or orally to mammalian hosts in an amount of from about 50 mg/day to about 20 g/day. Administration is generally carried out in divided doses, e.g., three to four times a day, analogous to dosing with a cephalosporin such as cefotaxime.

To illustrate the antibacterial properties of the compounds of the present invention, the following biological data is presented below.

IN VITRO ACTIVITY

Samples of the compounds prepared below in Examples 1–45 after solution in water and dilution with Nutrient Broth were found to exhibit the following ranges of Minimum Inhibitory Concentrations (MIC) versus the indicated microorganisms as determined by tube dilution. The MICs were determined using a broth microdilution assay in accordance with that recommended by the National Committee for Clinical Laboratory Standards (NCCLS). Mueller-Hinton medium was used except for Streptococci which was tested in Todd Hewitt broth. The final bacterial inocula contained approximately $5 \times 10^5$ cfu/ml and the plates were incubated at 35° C. for 18 hours in ambient air (Streptococci in 5% $CO_2$). The MIC was defined as the lowest drug concentration that prevented visible growth.

| Microorganism | MIC range in mcg/ml |
| --- | --- |
| S. pneumoniae A9585 | 0.001–0.03 |
| S. pyogenes A9604 | 0.0005–0.015 |
| E. faecalis A20688 | 0.25–8 |
| E. faecium A24885 | 0.25–4 |
| S. aureus penicillin-resistant A9537 | 0.003–0.06 |
| S. aureus penicillin-sensitive A15090 | 0.06–1 |
| S. epidermidis A24548 | 0.003–0.6 |
| S. epidermidis methicillin-resistant A25783 | 0.007–1 |

| Microorganism | MIC range in mcg/ml |
|---|---|
| *S. hemolyticus* A21638 | 0.003–2 |
| *S. hemolyticus* methicillin-resistant A27235 | 0.25–8 |

Samples of the compounds prepared in Examples 1–45 below after solution in water and dilution with Nutrient Agar were found to exhibit an MIC range of 0.25 to 8 mcg/mL against the representative MRSA strain A27223.

IN VIVO ACTIVITY

The in vivo therapeutic efficacy of the compounds prepared in Examples 1–45 below after intramuscular injection to mice experimentally infected with the representative MRSA strain A27223 was also measured.

The determination of the effectiveness of antimicrobial agents in *Staphylococcus aureus* systemic infection in mice Organisms: The test organism, MRSA strain A27223 used to generate systemic infection in mice, is grown on two large Brain Heart Infusion Agar plates. On each plate, 0.5 ml of frozen stock culture is plated out. Plates are then incubated for 18 hours at 30° C. The next day each plate is washed with 20 ml of Brain Heart Infusion Broth and then pooled together. A microscopic direct count of microorganism is done using a 1000 dilution of plate wash. After a direct count is obtained, the number of organisms per milliliter is calculated. The count is adjusted to the desired amount of inoculum by diluting in 4% hog mucin. The desired challenge (amount of organisms given to mice) is $2.4 \times 10^8$ cfu/0.5 ml/mouse for MRSA strain A27223. The mice are infected intraperitoneally with 0.5 ml of challenge. Ten non-treated infected mice are used as controls.

Mice: Mice used are male ICR mice. The average weight of the animals is from 20 to 26 grams.

Drug preparation and treatment: Compounds are tested at 4 dose levels, (25, 6.25, 1.56, and 0.39 mg/kg) and prepared in 5% cremophor, unless otherwise specified. Vancomycin is used as the control compound, and is dosed at 6.25, 1.56, 0.39, and 0.098 mg/kg. It is prepared in 0.1M phosphate buffer. There are five infected mice per dose level, and they are treated with 0.2 ml of the test compound, preferably by intramuscular injection. Treatment begins 15 minutes and 2 hours post-infection.

Test duration: A $PD_{50}$ (the dose of drug given which protects 50% of mice from mortality) runs for 5 days. During this time, mortality of mice are checked every day and deaths are recorded. The cumulative mortality at each dose level is used to calculate a $PD_{50}$ value for each compound. Surviving mice are sacrificed at the end of day 5 by $CO_2$ inhalation.

Calculation: Actual calculation of $PD_{50}$ is performed with a computer program using the Spearman-Karber procedure.

Results: The in vivo efficacy, expressed as the $PD_{50}$ value, ranged from about 0.4 to about 5 mg/kg (for certain compounds, more than one test was carried out; the indicated range is for at least one test result when multiple tests were done).

ILLUSTRATIVE EXAMPLES

The following examples illustrate the invention, but are not intended as a limitation thereof. The abbreviations used in the examples are conventional abbreviations well-known to those skilled in the art. Some of the abbreviations used are as follows:

| | |
|---|---|
| h = | hour(s) |
| mol = | mole(s) |
| mmol = | millimole(s) |
| min = | minute(s) |
| g = | gram(s) |
| THF = | tetrahydrofuran |
| L = | liter(s) |
| mL = | milliliter(s) |
| $Et_2O$ = | diethyl ether |
| MeOH = | methanol |
| DMF = | dimethylformamide |

In the following examples, all temperatures are given in degrees Centigrade. Melting points were determined on an electrothermal apparatus and are not corrected. Proton and carbon-13 nuclear magnetic resonance ($^1H$ and $^{13}C$ NMR) spectra were recorded on a Bruker AM-300 or a Varian Gemini 300 spectrometer. All spectra were determined in $CDCl_3$, DMSO-$d_6$, $CD_3OD$, or $D_2O$ unless otherwise indicated. Chemical shifts are reported in $\delta$ units relative to tetramethylsilane (TMS) and interproton coupling constants are reported in Hertz (Hz). Splitting patterns are designated as follows: s, singlet; d, doublet; t, triplet; q, quartet; m, multiplet; br, broad peak; dd, doublet of doublets and dt, doublet of triplets. Infrared spectra were determined on a Perkin-Elmer 1800 FT-IR spectrometer from 400 $cm^{-1}$, calibrated to 1601 $cm^{-1}$ absorption of a polystyrene film, and are reported in reciprocal centimeters ($cm^{-1}$). Mass spectra were recorded on a Kratos MS-50 or a Finnegan 4500 instrument utilizing direct chemical ionization (DCI, isobutene) or fast atom bombardment (FAB). Ultraviolet spectra were determined on a Hewlett Packard 8452 diode array spectrophotometer in the solvent indicated.

Analytical thin-layer chromatography (TLC) was carried out on precoated silica gel plates (60F-254) and visualized using UV light, iodine vapors, and/or staining by heating with methanolic phosphomolybdic acid. Column chromatography, also referred to as flash chromatography, was performed in a glass column using finely divided silica gel at pressures somewhat above atmospheric pressure with the indicated solvents. Reversed-phase analytical thin-layer chromatography was carried out on precoated reverse phase plates and visualized using UV light or iodine vapors. Reversed-phase column chromatography was performed in a glass column using Baker Octadecyl ($C_{18}$), 40 μm.

Example 1

1-[[(6R)-trans-2-Carboxy-8-oxo-
7-[2-(2,4,5-trichlorophenylthio)acetamido]-
5-thia-1-azabicyclo[4.2.0]-oct-2-en-3
-yl]methyl]-3-(aminocarbonyl)-pyridinium, inner
salt

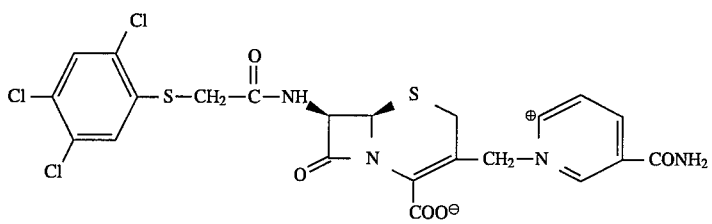

A. 2,4,5-Trichlorophenylthioacetic acid

A mixture of 2,4,5-trichlorothiophenol (9.98 g, 46.6 mmol) and bromoacetic acid (6.48 g, 46.6 mmol) in water (200 mL) was treated with 10N NaOH (11 mL) and then heated at 103° C. for 1 h. The reaction mixture was then cooled to 0° C. and acidified with 6N HCl. The product precipitated and was collected by filtration to give 12.0 g (95% yield) of white crystals, m.p. 101° C. $^1$H NMR ( 300 MHz, CDCl$_3$)δ 5 3.72 (s, 2 H), 7.49 (s, 1 H), 7.50 (s, 1 H). Anal. Calcd. for C$_8$H$_5$O$_2$SCl$_3$: C, 35.39; H, 1.86. Found: C, 35.33; H, 1.70.

B. (6R)-trans-3-Chloromethyl-7-[( 2,4,5-trichlorophenyl)thioacetamido-8-oxo-5-thia- 1-azabicyclo[4.2.0] oct-2-ene-2-carboxylate diphenylmethyl ester Procedure A. A solution of 2,4,5-trichlorophenylthioacetic acid (6.0 g, 22.1 mmol) in methylene chloride (30 mL) and thionyl chloride (10 mL, 137 mmol) was heated at reflux for 3 h. The reaction mixture was allowed to cool to room temperature and was concentrated in vacuo. The residue was evaporated two times from toluene (50 mL) to give 6.7 g of 2,4,5-trichlorophenylthioacetyl chloride as a pale yellow oil (100% yield). $^1$H NMR (300 MHz, CDCl$_3$) a 4.12 (s, 2 H), 7.54 (s, 1 H), 7.56 (s, 1 H). A solution of (6R)-trans-3-chloromethyl-7-amino-8-oxo-5-thia- 1-azabicyclo-[4.2.0] oct-2-ene-2-carboxylate, diphenylmethyl ester (4.15 g, 10 mmol) in THF (50 mL) was cooled to 0° C. and treated with N-methylmorpholine (1.2 g, 11.9 mmol) and 2,4,5-trichlorophenylthioacetyl chloride (3.3 g, 10.8 mmol). The reaction mixture was stirred for 1 h at 0° C., diluted with ethyl acetate (500 mL) and washed with water (500 mL). The organic solution was then dried (MgSO$_4$) and the solvents were evaporated in vacuo. The remaining residue was stirred with ether. The product solidified and was collected by filtration to give 4.5 g (60% yield) of title product as a white solid, m.p. 173° C. $^1$H NMR (300 MHz, CDCl$_3$)δ 3.45 (d, J=18.3 Hz, 1 H), 3.61 (d, J=18.3 Hz, 1 H), 3.68 (d, J=16.8 Hz, 1 H), 3.76 (d, J=16.8 Hz, 1 H), 4.37 (d, J=11.9 Hz, 1 H), 4.42 (d, J=11.9 Hz, 1 H), 4.98 (d, J=5.0 Hz, 1 H), 5.80 (dd, J=5.0, 8.9 Hz, 1 H), 6.99 (s, 1 H), 7.22 (d, J=8.9 Hz, 1 H), 7.30–7.45 (m, 10 H), 7.38 (s, 1 H), 7.51 (s, 1 H). Anal. Calcd. for C$_{29}$H$_{22}$N$_2$O$_4$S$_2$Cl$_4$: C, 52.11; H, 3.32; N, 4.19. Found: C, 52.06; H, 3.42; N, 4.19.

Procedure B. A solution of (6R)-trans-3-chloromethyl-7-amino- 8-oxo-5-thia-1-azabicyclo[4.2.0]oct- 2-ene-2-carboxylate, diphenylmethyl ester (28.3 g, 76.7 mmol) in THF (250 mL) was cooled to 0° C. and treated with dicyclohexylcarbodiimide (17.4 g, 84.4 mmol). The resulting solution was treated with 2,4,5-trichlorophenylthioacetic acid (20.8 g, 76.7 mmol) in a single portion. Within 5 min, a solid began to form. Additional THF (150 mL) was added and the reaction mixture was stirred at 0° C. for 2 h. The mixture was then filtered to remove insoluble material and the filtrate was concentrated in vacuo. The residue was slurried in CH$_2$Cl$_2$ (300 mL) for 1 h, then diethyl ether (1 L) was added and the solid was collected by filtration to give 41.8 g (88% yield) of title product as a white solid. Analytical data was consistent with that for the material prepared by Procedure A.

C. (6R)-trans-3-Chloromethyl-7-[( 2,4,5-trichlorophenyl)thioacetamido-8-oxo-5-thia- 1-azabicyclo[4.2.0] oct-2-ene-2-carboxylic acid A mixture of the cephem acid prepared in Step B above (10.0 g, 13.2 mmol) in CH$_2$Cl$_2$ (200 mL) at 0° C. was treated with anisole (24 mL) and trifluoroacetic acid (80 mL). The resulting solution was stirred at 0° C. for 1 h and the solvents were then evaporated in vacuo. The residue was triturated with ether and the solid was collected by filtration. The product was stirred with ethyl acetate (100 mL) and collected by filtration to give 6.1 g of an off white solid (90% yield), m.p. 120° C. $^1$H NMR (300 MHz, DMSO-d$_6$)δ 3.53 (d, J=17.9 Hz, 1 H), 3.72 (d, J=17.9 Hz, 1 H), 3.95 (s, 2 H), 4.54 (d, J=11.3 Hz, 1 H), 4.59 (d, J=11.3 Hz, 1 H), 5.15 (d, J=4.9 Hz, 1 H), 5.71 (dd, J=4.9, 8.2 Hz, 1 H), 7.68 (s, 1 H), 7.86 (s, 1 H), 9.28 d, J=8.2 Hz, 1 H). Anal. Calcd. for C$_{16}$H$_{12}$N$_2$O$_4$S$_2$Cl$_4$·0.2 C$_4$H$_{10}$O: C, 39.03; H, 2.73; N, 5.42. Found: C, 39.05; H, 2.92; N, 5.48.

D. 1-[[((6R)-trans-2-Carboxy-8-oxo- 7-[2-(2,4,5-trichlorophenylthio)acetamido]- 5-thia-1-azabicyclo4.2.0]-oct-2-en-3-yl]methyl]-3-(aminocarbonyl)pyridinium, inner salt A solution of (6R)-trans-3-chloromethyl-7-[( 2,4,5-trichlorophenyl)-thio-acetamido-8-oxo-5-thia- 1-azabicyclo[4.2.0]oct-2-ene-2-carboxylic acid (6.0 g, 11.9 mmol) in THF (80 mL) at 0° C. was treated with nicotinamide (2.9 g, 23.8 mmol) and then sodium iodide (1.8 g, 11.9 mmol) in acetone (12 mL) was added. The resulting solution was stirred for 1 h at 0° C. and then for 1 h at 20° C. The solvents were stirred with diethyl ether (100 mL) and the solid was collected by filtration. The solid was slurried in ethyl acetate (50 mL) and then acetone (50 mL) to give 3.5 g of a pale yellow solid. This solid was dissolved in H$_2$O (100 mL), methanol (100 mL) and 6N HCl (5 mL) at 0° C. The methanol was removed in vacuo to give 3.05 g of the product (41% yield) as a pale yellow solid, m.p. 148° C. $^1$H NMR (300 MHz, DMSO-d$_6$) δ 3.22 (d, J=18 Hz, 1 H), 3.50 (d, J=18 Hz, 1 H), 3.90 (s, 2 H), 5.04 (d, J=5 Hz, 1 H), 5.31 (d, J=14 Hz, 1 H), 5.64 (dd, J=8, 5 Hz, 1 H), 5.69 (d, J=14 Hz, 1 H), 7.65 (s, 1 H), 7.83 (s, 1 H), 8.16 (m, 1 H), 8.29 (dd, J =8, 6 Hz, 1 H) 8.60 (s, 1 H), 8.94 (d, J=8 Hz, 1 H), 9.26 (d, J=8 Hz, 1 H), 9.51 (d, J=6 Hz, 1 H), 9.62 (s, 1 H); IR (KBr) 1782, 1688 cm$^{-1}$; FAB MS m/z 586 (M$^+$). Exact Mass: Calcd for C$_{22}$H$_{18}$ N$_4$O$_5$S$_2$Cl$_3$: 586.9784. Found: 586.9776.

Example 2

1-[[((6R)-trans-2-Carboxy-8-oxo-
7-[2-(2,4,5-trichlorophenylthio)acetamido]-
5-thia-1-azabicyclo[4.2.0]-oct-2-en-
3-yl]methyl]-3-(aminomethylcarbonyl-amino)pyridinium
trifluoroacetate, inner salt

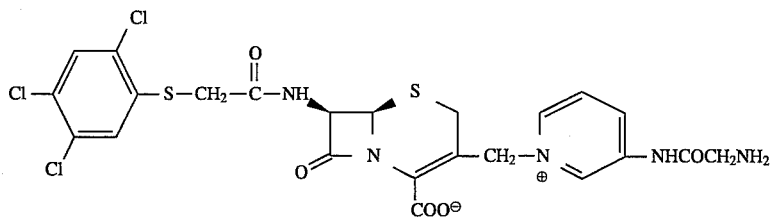

A solution of (6R)-trans-3-Chloromethyl-7-[( 2,4,5-trichlorophenyl)-thioacetamido-8-oxo-5-thia- 1-azabicyclo [4.2.0]oct-2-ene-2-carboxylic acid (0.602 g, 1.20 mmol) in anhydrous DMF (4 mL) was cooled to 0° C. and treated sequentially with 3-[(butyloxycarbonylamino)methyl-carbonyl-amino]pyridine (0.603 g, 2.4 mmol; ref: G. Hess et al., *J. Org. Chem.* 1993, 58, 4599–4605) and sodium iodide (0.180 g, 1.20 mmol). The reaction mixture was stirred at 0° C. for 2 h and then at room temperature for 2 h. Water (80 mL) was added and after 30 min, the resulting solid was collected by filtration. The solid was slurried in ethyl acetate (15 mL) for 1 h, collected by filtration, slurried in acetone (10 mL) for 1 h, and then collected again by filtration to give 0.348 g of a yellow solid. The solid was dissolved in $CH_2Cl_2$ (15 mL) and the solution was cooled to 0° C. Anisole (1.75 mL) was added, followed by addition of trifluoroacetic acid (6.0 mL). The reaction mixture was stirred at 0° C. for 1 h and then concentrated in vacuo. The residue was slurried in diethyl ether (75 mL) at room temperature for 30 min, and the resulting solid was collected by filtration to provide 0.342 g of the product as a yellow solid (40% from (6R)-trans-3-chloromethyl-7-[( 2,4,5-trichlorophenyl)-thioacetamido-8-oxo-5-thia- 1-azabicyclo[4.2.0]oct-2-ene-2-carboxylic acid).

$^1$H NMR (300 MHz, DMSO-$d_6$) δ 3.32 (d, J=18 Hz, 1 H), 3.54 (d, J=18 Hz, 1 H), 3.91 (s, 2 H), 3.94 (br s, 2 H), 5.11 (d, J=5 Hz, 1 H), 5.47 (d, J=14 Hz, 1 H), 5.70 (d, J=14 Hz, 1 H), 5.75 (dd, J=5, 8 Hz, 1 H), 7.48 (s, 1 H), 7.65 (s, 1 H), 7.85 (s, 1 H), 8.17 (dd, J=6, 8 Hz, 1 H), 8.35 (br, $NH_3$), 8.54 (d, J=8 Hz, 1 H), 8.87 (d, J=6 Hz, 1 H), 9.24 (d, J=8 Hz, 1 H), 9.45 (s, 1 H); $^{13}$C NMR (75 MHz, DMSO-$d_6$) δ 15.16, 24.94, 34.23, 41.18, 57.18, 59.46, 127.93, 128.27, 128.75, 129.71, 130.38, 130.69, 134.57, 134.70, 136.70, 138.68, 140.33, 157.96, 162.88, 164.07, 166.57, 168.16; IR (KBr) 1790, 1675, 1630 $cm^{-1}$; FAB MS m/z 582 (MH$^+$).

The following compounds were prepared according to the general procedures of Example 1 and 2 by varying the thiol starting material and the pyridine derivative:

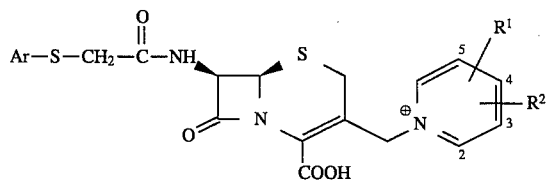

| Ex. No. | Ar | R$^1$ | R$^2$ | Isolated As |
|---|---|---|---|---|
| 3 | 2,5-dichlorophenyl | 3-CONH$_2$ | H | HCl salt |
| 4 | 3-bromophenyl | 3-CONH$_2$ | H | Zwitterion |
| 5 | 2,5-dimethyl-4-chlorophenyl | 3-CONH$_2$ | H | Zwitterion |
| 6 | 2,4,5-trichlorophenyl | 3-CONHCH$_3$ | H | Zwitterion |
| 7 | 2,5-dichlorophenyl | 3-CONHCH$_2$OH | H | Zwitterion |
| 8 | 2,4,5-trichlorophenyl | 3-CONHCH$_2$OH | H | HI |
| 9 | 2,5-dichlorophenyl | 3-CONHCH$_2$CH$_2$NH$_2$ | H | HCl |
| 10 | 2,4,5-trichlorophenyl | 3-CONHCH$_2$CH$_2$NH$_2$ | H | Trifluoroacetate |
| 11 | 3-bromophenyl | 3-CONHCH$_2$CH$_2$NH$_2$ | H | Trifluoroacetate |
| 12 | 2-chloro-5-trifluoromethylphenyl | 3-CONHCH$_2$CH$_2$NH$_2$ | H | mixed HI/ trifluoroacetate |
| 13 | 1-naphthyl | 3-CONHCH$_2$CH$_2$NH$_2$ | H | Trifluoroacetate |
| 14 | 2-benzthiazolyl | 3-CONHCH$_2$CH$_2$NH$_2$ | H | Trifluoroacetate |
| 15 | 2,5-dichlorophenyl | 3-CONH(CH$_2$)$_3$NH$_2$ | H | Trifluoroacetate |
| 16 | 2,4,5-trichlorophenyl | 3-COCH$_3$ | H | HCl |
| 17 | 2,4,5-trichlorophenyl | 3-CN | H | HCl |
| 18 | 2,5-dichlorophenyl | 3-CH$_2$NH$_2$ | H | Trifluoroacetate |
| 19 | 2,4,5-trichlorophenyl | 3-CH$_2$NH$_2$ | H | Trifluoroacetate |
| 20 | 2-chloro-5-trifluoromethylphenyl | 3-CH$_2$NH$_2$ | H | Trifluoroacetate |
| 21 | 2,5-dichlorophenyl | 3-CH$_2$OH | H | Zwitterion |
| 22 | 2,4,5-trichlorophenyl | 3-CH$_2$OH | H | Zwitterion |
| 23 | 2,5-dichlorophenyl | 3-CH$_2$CONH$_2$ | H | Zwitterion |
| 24 | 2,5-dichlorophenyl | 3-NHCONH$_2$ | H | Zwitterion |
| 25 | 2,4,5-trichlorophenyl | 3-NHCONH$_2$ | H | Zwitterion |
| 26 | 2,5-dichlorophenyl | 3-NHCOCH$_2$NH$_2$ | H | Trifluoroacetate |
| 27 | 2,5-dichlorophenyl | 2-NHCO(CH$_2$)$_2$NH$_2$ | H | Trifluoroacetate |
| 28 | 2,5-dichlorophenyl | 4-CONH$_2$ | H | HI |
| 29 | 2,4,5-trichlorophenyl | 4-CONH$_2$ | H | HI |
| 30 | 2,5-dichlorophenyl | 4-CONHCH$_2$CH$_2$NH$_2$ | H | Trifluoroacetate |
| 31 | 2,4,5-trichlorophenyl | 4-CONHCH$_2$CH$_2$NH$_2$ | H | Trifluoroacetate |
| 32 | 2,5-dichlorophenyl | 4-CH$_2$NH$_2$ | H | HCl |

-continued

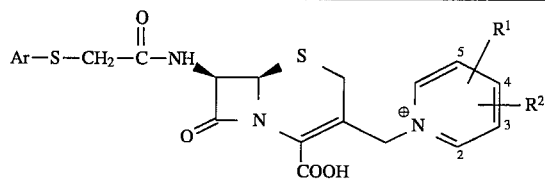

| Ex. No. | Ar | R¹ | R² | Isolated As |
|---|---|---|---|---|
| 33 | 2,5-dichlorophenyl | 4-CH₂OH | H | Zwitterion |
| 34 | 2,4,5-trichlorophenyl | 2-CH₂NH₂ | H | Trifluoroacetate |
| 35 | 2,5-dichlorophenyl | 2-CH₂OH | H | Zwitterion |
| 36 | 2,4,5-trichlorophenyl | 2-CH₂CH₂NH₂ | H | Trifluoroacetate |
| 37 | 2,5-dichlorophenyl | 2-CH₂CH₂OH | H | Zwitterion |
| 38 | 2,5-dichlorophenyl | 3-CONHCH₂CH(OH)CH₂NH₂ | H | Trifluoroacetate |
| 39 | 2,5-dichlorophenyl | 3-CON⟨piperazinyl⟩NH | H | Trifluoroacetate |
| 40 | 2,5-dichlorophenyl | 3-NHCONH(CH₂)₂NH₂ | H | Acetate |
| 41 | 2,5-dichlorophenyl | 3-NH—C(O)—prolyl | H | Trifluoroacetate |
| 42 | 2,5-dichlorophenyl | 3-NH—C(O)—CH(NH₂)CH₂OH | H | Trifluoroacetate |
| 43 | 2,5-dichlorophenyl | 3-CH₂CONH(CH₂)₂NH₂ | H | Trifluoroacetate |
| 44 | 2,5-dichlorophenyl | 4-CH₂NHCOCH₂NH₂ | H | Trifluoroacetate |
| 45 | 2,5-dichlorophenyl | 3-NHCOCH₂CH(OH)CH₂NH₂ | H | Trifluoroacetate |

The ¹H NMR and FAB MS characterizing properties for the compounds of Examples 1–45 are shown below in Table I and II.

TABLE I

NMR DATA

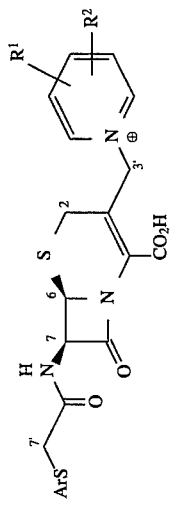

| Cmpd of Ex. No | H-2 | H-6 | H-7 | H-3' | H-7' | NH | Ar | PyrH | $R^1, R^2, R^3$ |
|---|---|---|---|---|---|---|---|---|---|
| 1 | 3.50 (d, J = 18) 3.15 (d, J = 18) | 5.03 (d, J = 5) | 5.59 (dd, J = 5,8) | 5.70 (d, J = 14) 5.23 (d, J = 14) | 3.87 (s) | 9.23 (d, J = 8) | 7.44 (dd, J = 2,8) 7.21 (dd, J = 2,8) | 9.64 (s) 9.62 (d, J = 6) 8.91 (d, J = 8) 8.29 (dd, J = 8,6) | 8.54 (s) 8.15 (s) |
| 2 | 3.54 (d, J = 18) 3.32 (d, J = 18) | 5.11 (d, J = 5) | 5.75 (dd, J = 5,8) | 5.70 (d, J = 14) 5.47 (d, J = 14) | 3.91 (s) | 9.24 (d, J = 8) | 7.85 (s) 7.65 (s) | 8.87 (d, J = 7) 8.54 (d, J = 9) 8.17 (dd, J = 7,9) 7.48 (s) | 8.34 (—NH$_3$) 3.94 (br s) |
| 3 | 3.50 (d, J = 18) 3.22 (d, J = 18) | 5.04 (d, J = 5) | 5.64 (dd, J = 5,8) | 5.69 (d, J = 14) 5.31 (d, J = 14) | 3.90 (s) | 9.26 (d, J = 8) | 7.83 (s) 7.65 (s) | 9.62 (s) 9.51 (d, J = 6) 8.94 (d, J = 8) 8.29 (dd, J = 6,8) | 8.60 (s) 8.16 (s) |
| 4 | 3.53 (d, J = 18) 3.25 (d, J = 18) | 5.05 (d, J = 5) | 5.64 (dd, J = 5,8) | 5.70 (d, J = 14) 5.34 (d, J = 14) | 3.77–3.83 (m) | 9.22 (d, J = 8) | 7.53 (s) 7.32 (m) 7.21 (t, J = 8) | 9.67 (s) 9.48 (d, J = 6) 8.96 (d, J = 8) 8.30 (t, J = 7) | 8.70 (s) 8.16 (s) |
| 5 | 3.48 (d, J = 18) 3.23 (d, J = 18) | 5.00 (d, J = 5) | 5.59–5.66 (m, overlaps with H-3') | 5.59–5.66 (m, overlaps with H-7) 5.32 (d, J = 14) | 3.66–3.74 (m) | 9.16 (d, J = 8) | 7.19 (s) 7.16 (s) 2.16 (s) 2.14 (s) | 9.60 (s) 9.40 (d, J = 5) 8.91 (d, J = 8) 8.25 (t, J = 7) | 8.66 (s) 8.11 (s) |
| 6 | 3.53 (d, J = 18) 3.21 (d, J = 18) | 5.06 (d, J = 5) | 5.62 (dd, J = 5,8) | 5.72 (d, J = 13) 5.31 (d, J = 13) | 3.92 (s) | 9.26 (d, J = 8) | 7.83 (s) 7.66 (s) | 9.62 (m) 8.87 (d, J = 8) 8.30 (t, J = 8) | 9.14 (NH) 2.51 (s, Me) |
| 7 | 3.54 (d, J = 18) 3.21 (d, J = 18) | 5.05 (d, J = 5) | 5.62 (dd, J = 5,8) | 5.74 (d, J = 13) 5.29 (d, J = 13) | 3.90 (s) | 9.22 (d, J = 8) | 7.48 (dd, J = 2,8) 7.23 (dd, J = 2,8) | 9.75 (m) 8.92 (d, J = 8) 8.30 (dd, J = 8,8) | 9.75 (m, NH) 4.77 (d, J = 6) |
| 8 | 3.51 (d, J = 18) 3.13 (d, J = 18) | 5.01 (d, J = 5) | 5.56 (dd, J = 5,8) | 5.74 (d, J = 14) 5.19 (d, J = 14) | 3.89 (s) | 9.25 (d, J = 8) | 7.83 (s) 7.66 (s) | 9.60 (s) 9.45 (d, J = 8) 8.91 (d, J = 7) 8.30 (t, J = 7,8) | 4.78 (br s, CH$_2$) |
| 9 | 3.57 (d, J = 18) 3.47 (d, J = 18) | 5.16 (d, J = 5) | 5.78 (dd, J = 5,8) | 5.64 (br s) | 3.90 (s) | 9.30 (s) | 7.45 (m) 7.22 (dd, J = 2,8) | 9.61 (s) 9.18 (m) 8.30 (t) | 9.81 (t, NH) 8.25 (br s) 3.60 (m) 3.04 (m) |
| 10 | 3.50 (d, J = 18) 3.21 (d, J = 18) | 5.12 (d, J = 5) | 5.76 (dd, J = 5,8) | 5.69 (d, J = 14) 5.54 (d, J = 14) | 3.92 (s) | 9.27 (d, J = 8) | 7.85 (s) 7.65 (s) | 9.51 (s) 9.27 (d, J = 8) | 9.34 (t, NH) 7.91 (br s) |

TABLE I-continued

NMR DATA

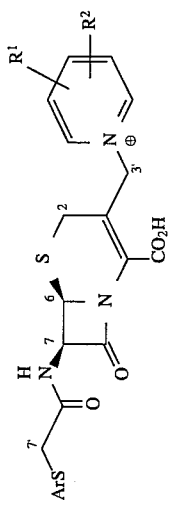

| Cmpd of Ex. No | H-2 | H-6 | H-7 | H-3' | H-7' | NH | Ar | PyrH | R¹, R², R³ |
|---|---|---|---|---|---|---|---|---|---|
| 11 | 3.53 (d, J = 18)<br>3.31 (d, J = 18) | 5.09 (d, J = 5) | 5.69–5.72 (m, overlaps with H-3') | 5.69–5.72 (m, overlaps with H-7) | 3.79 (s) | 9.22 (d, J = 8) | 7.53 (s)<br>7.30–7.35 (m)<br>7.22 (d, J = 8) | 8.96 (d, J = 9)<br>8.36 (dd, J = 8,9)<br>9.62 (s)<br>9.35 (d, J = 6)<br>9.00 (d, J = 8) | 3.57 (m)<br>3.03 (m)<br>9.62 (s)<br>8.16 (s)<br>3.05 (s) |
| 12 | 3.36–3.48 (m, overlaps with H₂O) | 5.13 (d, J = 5) | 5.78 (dd, J = 5,8) | 5.44 (d, J = 14)<br>5.67 (d, J = 14)<br>5.56 (d, J = 15) | 3.96 (s) | 9.29 (d, J = 8) | 7.77 (s)<br>7.67–7.70 (m)<br>7.52–7.55 (m) | 8.34 (t, J = 7)<br>9.47 (s)<br>9.19 (d, J = 6)<br>8.97 (d, J = 8)<br>8.36 (dd, J = 6,8) | 3.58 (m)<br>9.34 (m)<br>7.90 (s)<br>3.55–3.47 (m)<br>3.01–3.03 (m) |
| 13 | 3.51 (d, J = 18)<br>3.21 (d, J = 18) | 5.02 (d, J = 5) | 5.62 (dd, J = 5,8) | 5.63 (d, J = 12)<br>5.24 (d, J = 12) | 3.81 (s) | 9.21 (d, J = 8) | 8.17 (d, J = 9)<br>7.91 (d, J = 9)<br>7.77 (d, J = 8)<br>7.54 (m, 3H)<br>7.40 (d, J = 8) | 9.72 (s)<br>9.61 (m)<br>8.89 (m)<br>8.35 (m) | 9.45 (m,NH)<br>7.99 (m)<br>3.53 (br s, CH₂)<br>3.03 (br s, CH₂) |
| 14 | 3.51 (d, J = 17)<br>3.18 (d, J = 17) | 5.04 (d, J = 5) | 5.64–5.68 (m, overlaps with H-3' doublet | 5.65 (d, overlaps with H-7 m)<br>5.24 (d, J = 14) | 4.18 (s) | 9.30 (d, J = 8) | 7.97 (d, J = 8)<br>7.80 (d, J = 8)<br>7.42 (d, J = 8)<br>7.33 (d, J = 8) | 9.73 (s)<br>9.52 (m)<br>8.91 (d, J = 9)<br>8.30 (d, J = 7) | 9.46 (br s,NH)<br>8.02 (br s,<br>NH₃+) 3.45<br>(br s,CH₂)<br>3.02 (br s, CH₂) |
| 15 | 3.53 (d, J = 18)<br>3.21 (d, J = 18) | 5.05 (d, J = 5) | 5.65 (dd, J = 5,8) | 5.70 (d, J = 14)<br>5.31 (d, J = 14) | 3.88 (s) | 9.27 (d, J = 8) | 7.45 (m)<br>7.22 (dd, J = 2,8) | 9.72 (s)<br>9.51 (d, J = 5)<br>8.92 (d, J = 7) | 9.43 (s)<br>7.86 (br s)<br>2.89 (m) |
| 16 | 3.52 (d, J = 18)<br>3.41 (d, J = 18) | 5.14 (d, J = 5) | 5.77 (dd, J = 5,8) | 5.70 (d, J = 15)<br>5.62 (d, J = 15) | 3.93 (s) | 9.28 (d, J = 8) | 7.85 (s)<br>7.65 (s) | 8.29 (dd, J = 5,7)<br>9.62 (s)<br>9.21 (d, J = 6)<br>9.08 (d, J = 8) | 1.85 (m)<br>2.74 (s) |
| 17 | 3.48 (br s) | 5.11 (d, J = 5) | 5.79 (dd, J = 5,8) | 5.63 (br s) | 3.94 (s) | 9.28 (d, J = 8) | 7.85 (s)<br>7.65 (s) | 8.36 (dd, J = 6,8)<br>9.78 (s)<br>9.27 (d, J = 8)<br>9.15 (d, J = 8) | — |
| 18 | 3.50 (d, J = 18)<br>3.21 (d, J = 18) | 5.02 (d, J = 5) | 5.60 (dd, J = 5,8) | 5.64 (d, J = 14)<br>5.23 (d, J = 14) | 3.89 (s) | 9.23 (d, J = 8) | 7.46 (m)<br>7.22 (dd, J = 2,8) | 8.40 (dd, J = 8,8)<br>9.47 (d, J = 7)<br>9.32 (s)<br>8.64 (d, J = 8) | 4.25 (s) |
| 19 | 3.48 (d, J = 18) | 5.05 (d, J = 5) | 5.65 (dd, J = 5,8) | 5.62 (d, J = 14) | 3.92 (s) | 9.28 (d, J = 8) | 7.83 (s) | 8.25 (t, J = 7,8)<br>9.30 (d, J = 6) | 4.29 (s) |

TABLE I-continued

NMR DATA

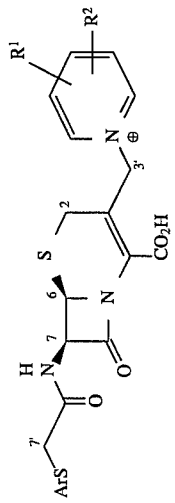

| Cmpd of Ex. No | H-2 | H-6 | H-7 | H-3' | H-7' | NH | Ar | PyrH | $R^1, R^2, R^3$ |
|---|---|---|---|---|---|---|---|---|---|
| | 3.25 (d, J = 18) | | | 5.42 (d, J = 14) | | | 7.64 (s) | 9.25 (s) 8.69 (d, J = 8) 8.27 (dd, J = 6,8) | |
| 20 | 3.48 (d, J = 18) 3.22 (d, J = 18) | 5.05 (d, J = 5) | 5.67 (dd, J = 5,8) | 5.62 (d, J = 14) 5.37 (d, J = 14) | 3.95 (s) | 9.27–9.29 (m overlaps with pyrH) | 7.77 (s) 7.67 (d, J = 8) 7.51 (d, J = 8) | 9.27–9.29 (m overlaps with pyrH) 8.70 (d, J = 8) 8.27 (t, J = 7) | 4.29 (s) |
| 21 | 3.53 (d, J = 18) 3.39 (d, J = 18) | 5.15 (d, J = 5) | 5.79 (dd, J = 5,8) | 5.62 (d, J = 14) 5.54 (d, J = 14) | 3.91 (s) | 9.28 (d, J = 8) | 7.47 (m) 7.24 (dd, J = 2,8) | 9.00 (s) 8.92 (d, J = 6) 8.55 (d J = 8) 8.16 (dd, J = 6,8) | 4.75 (s) |
| 22 | 3.51 (d, J = 18) 3.15 (d, J = 18) | 5.05 (d, J = 5) | 5.62 (dd, J = 5,8) | 5.67 (d, J = 14) 5.28 (d, J = 14) | 3.90 (s) | 9.24 (d, J = 8) | 7.84 (s) 7.66 (s) | 9.22 (m) 8.52 (d, J = 8) 8.14 (dd, J = 6,8) | 4.72 (s) |
| 23 | 3.53 (d, J = 18) 3.08 (d, J = 18) | 5.03 (d, J = 5) | 5.58 (dd, J = 5,8) | 5.70 (d, J = 14) 5.15 (d, J = 14) | 3.89 (s) | 9.24 (d, J = 8) | 7.47 (m) 7.23 (dd, J = 2,8) | 9.44 (d, J = 6) 9.33 (s) 8.49 (d, J = 8) 8.13 (dd, J = 6,8) | 3.74 (s) |
| 24 | 3.52 (d, J = 18) 3.02 (d, J = 18) | 5.06 (d, J = 5) | 5.62 (dd, J = 5,8) | 5.77 (d, J = 14) 5.15 (d, J = 14) | 3.87 (s) | 9.26 (d, J = 8) | 7.46 (m) 7.21 (dd, J = 2,8) | 9.25 (s) 8.81 (d, J = 6) 8.68 (d, J = 8) 7.95 (dd, J = 6,8) | 6.85 (br s, $NH_2$) |
| 25 | 3.52 (d, J = 18) 2.98 (d, J = 18) | 5.06 (d, J = 5) | 5.60 (dd, J = 5,8) | 5.81 (d, J = 13) 5.11 (d, J = 13) | 3.89 (s) | 9.28 (d, J = 8) | 7.83 (s) 7.67 (s) | 9.24 (m) 8.79 (d, J = 5) 8.73 (d, J = 8) 7.97 (dd, J = 5,8) | 6.90 (br s, $NH_2$) |
| 26 | 3.55 (d, J = 18) 3.38 (d, J = 18) | 5.13 (d, J = 5) | 5.78 (dd, J = 5,8) | 5.69 (d, J = 14) 5.50 (d, J = 14) | 3.90 (s) | 9.24 (d, J = 8) | 7.46 (m) 7.24 (dd, J = 2,8) | 9.45 (s) 8.84 (d, J = 6) 8.53 (d, J = 8) 8.18 (dd, J = 6,8) | 8.35 ($-NH_3$) 3.94 (br s) |
| 27 | 3.54 (d, J = 18) 3.22 (d, J = 18) | 5.07 (d, J = 5) | 5.68 (dd, J = 5,8) | 5.72 (d, J = 14) 5.35 (d, J = 14) | 3.90 (s) | 9.19 (d, J = 8) | 7.24 (dd, J = 2,8) 7.47 (m) | 9.58 (s) 9.00 (d, J = 6) 8.55 (d, J = 8) 8.12 (dd, J = 6,8) | 7.89 (br s) 3.82 (m) 3.15 (m) |
| 28 | 3.53 (d, J = 17) 3.18 (d, J = 17) | 5.05 (d, J = 5) | 5.63 (dd, J = 5,8) | 5.70 (d, J = 13) 5.28 (d, J = 13) | 3.89 (s) | 9.29 (d, J = 8) | 7.47 (m) 7.23 (dd, J = 2,8) | 9.50 (d, J = 6) 8.47 (d, J = 6) | 8.76 (br s) 8.27 (br s) |

TABLE I-continued

NMR DATA

| Cmpd of Ex. No | H-2 | H-6 | H-7 | H-3' | H-7' | NH | Ar | PyrH | R¹, R², R³ |
|---|---|---|---|---|---|---|---|---|---|
| 29 | 3.52 (d, J = 18)<br>3.22 (d, J = 18) | 5.06 (d, J = 5) | 5.65 (dd, J = 5,8) | 5.68 (d, J = 14)<br>5.34 (d, J = 14) | 3.91 (s) | 9.24 (d, J = 8) | 7.84 (s)<br>7.66 (s) | 9.42 (d, J = 6)<br>8.47 (d, J = 6) | 8.71 (br s)<br>8.28 (br s) |
| 30 | 3.54 (d, J = 18)<br>3.16 (d, J = 18) | 5.05 (d, J = 4) | 5.65 (dd, J = 5,8) | 5.68 (d, J = 16)<br>5.25 (d, J = 16) | 3.89 (s) | 9.31 (d, J = 8) | 7.44 (s)<br>7.21 (s) | 9.51 (br s)<br>8.53 (br s) | 10.0 (br s)<br>8.16 (br s)<br>3.55 (br s)<br>3.02 (br s) |
| 31 | 3.56 (d, J = 18)<br>3.18 (d, J = 18) | 5.07 (d, J = 5) | 5.65 (dd, J = 5,8) | 5.72 (d, J = 14)<br>5.30 (d, J = 14) | 3.92 (s) | 9.26 (d, J = 8) | 7.89 (s)<br>7.66 (s) | 9.51 (d, J = 6)<br>8.52 (d, J = 6) | 8.03 (br s)<br>3.64 (m)<br>3.05 (m) |
| 32 | 3.53 (d, J = 18)<br>3.41 (d, J = 18) | 5.15 (d, J = 5) | 5.78 (dd, J = 5,8) | 5.58 (br s) | 3.91 (s) | 9.31 (d, J = 8) | 7.46 (m)<br>7.23 (dd, J = 2,8) | 9.08 (d, J = 6)<br>8.32 (d, J = 6) | 4.41 (s) |
| 33 | 3.50 (d, J = 18)<br>3.05 (d, J = 18) | 5.02 (d, J = 5) | 5.57 (dd, J = 5,8) | 5.60 (d, J = 14)<br>5.14 (d, J = 14) | 3.87 (s) | 9.24 (d, J = 8) | 7.44 (m)<br>7.21 (dd, J = 2,8) | 9.25 (d, J = 6)<br>8.03 (d, J = 6) | 4.79 (s) |
| 34 | 3.45 (d, J = 18)<br>3.37 (d, J = 18) | 5.11 (d, J = 5) | 5.79 (dd, J = 5,8) | 5.62 (br s) | 3.94 (s) | 9.27 (d, J = 8) | 7.85 (s)<br>7.65 (s) | 9.14 (s)<br>9.05 (d, J = 6)<br>8.71 (d, J = 8)<br>8.30 (dd, J = 6,8) | 8.57(br s, —NH₃)<br>4.31 (br s) |
| 35 | 3.40 (d, J = 18)<br>3.09 (d, J = 18) | 5.03 (d, J = 5) | 5.60 (dd, J = 5,8) | 5.45 (d, J = 14)<br>5.35 (d, J = 14) | 3.90 (s) | 9.24 (d, J = 8) | 7.47 (m)<br>7.22 (dd, J = 2,8) | 9.26 (m)<br>8.57 (m)<br>8.19 (d, J = 6)<br>8.07 (m) | 4.94 (br s) |
| 36 | 3.50 (d, J = 18)<br>3.38 (d, J = 18) | 5.17 (d, J = 5) | 5.79 (dd, J = 5,8) | 5.65 (d, J = 14)<br>5.57 (d, J = 14) | 3.95 (s) | 9.30 (d, J = 8) | 7.87 (s)<br>7.67 (s) | 8.88 (d, J = 8)<br>8.62 (t, J = 8)<br>8.09 (m,) | 8.02 (br s)<br>3.42 (m)<br>3.25 (m) |
| 37 | 3.41 (d, J = 17)<br>3.05 (d, J = 17) | 5.01 (d, J = 5) | 5.59 (dd, J = 5,8) | 5.52 (br s) | 3.90 (s) | 9.23 (d, J = 8) | 7.45 (m)<br>7.22 (dd, J = 2,8) | 9.36 (d, J = 6)<br>8.49 (m)<br>8.04 (m) | 3.80 (m)<br>3.45 (m) |
| 38 | 3.53 (d, J = 18)<br>3.18 (d, J = 18) | 5.03 (d, J = 5) | 5.59 (dd, J = 5,8) | 5.70 (d, J = 16)<br>5.25 (br s) | 3.87 (s) | 9.21 (d, J = 8) | 7.44 (m)<br>7.21 (m) | 8.29 (t, J = 8)<br>8.91 (t, J = 8)<br>9.31 (br s)<br>9.57 (br s) | 9.7 (s, —NH)<br>7.87 (br s, —NH₂)<br>2.72 (br s)<br>2.9 (br s) |
| 39 | 3.53 (d, J = 18)<br>3.20 (br s) | 5.04 (d, J = 5) | 5.59–5.62 (m) overlaps w/3' doublet | 5.29 (d, J = 15)<br>5.60 (m) overlaps w/H-7 | 3.87 (s) | 9.20 (d = 8) | 7.44 (s)<br>7.22 (dd, J = 2,8) | 8.26 (t, J = 7)<br>8.67 (t, J = 7)<br>9.38 (br s)<br>9.62 (br s) | 3.88 (br s)<br>8.97 (br s —NH)<br>3.8 (s)<br>3.19 (br s) |
| 40 | 3.14 (d, J = 19) | 5.02 (d, J = 5) | 5.61 (d, J = 5) | 5.17 (d, J = 15) | 3.67 (s) | — | 6.94 (m) | 7.75 (m) | 3.31 (m) |

TABLE I-continued

NMR DATA

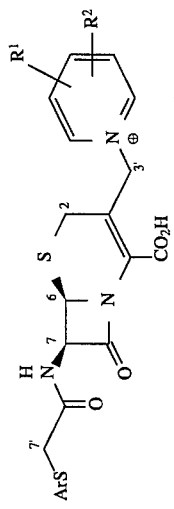

| Cmpd of Ex. No | H-2 | H-6 | H-7 | H-3' | H-7' | NH | Ar | PyrH | R¹, R², R³ |
|---|---|---|---|---|---|---|---|---|---|
|  | 3.47 (d, J = 19) |  |  | 5.92 (d, J = 15) |  |  | 7.10 (m) | 8.12 (m)<br>8.42 (m)<br>9.39 (s) | 3.59 (m) |
| 41 | 3.23 (d, J = 18)<br>3.53 (d, J = 18) | 5.05 (d, J = 5) | 5.68 (dd, J = 5,8) | 5.70 (d, J = 14)<br>5.36 (d, J = 14) | 3.89 (br s) | 9.23 (d, J = 8) | 7.22 (d, J = 8)<br>7.45 (m) | 8.14 (dd, J = 5,8)<br>8.59 (d, J = 8)<br>8.98 (d, J = 5)<br>9.67 (br s) | 4.48 (m)<br>3.36 (m)<br>2.40 (m)<br>1.96 (m) |
| 42 | 3.08 (d, J = 18)<br>3.49 (d, J = 18) | 5.01 (d, J = 5) | 5.59 (dd, J = 5,8) | 5.65 (d, J = 13)<br>5.21 (d, J = 13) | 3.86 (s) | 9.17 (d = 8) | 7.21 (dd, J = 2,8)<br>7.43 (m) | 8.05 (m)<br>8.60 (d, J = 8)<br>9.03 (d, J = 5)<br>9.63 (s) | 4.16 (m)<br>3.83 (m) |
| 43 | 3.57 (d, J = 18)<br>3.26 (d, J = 18) | 5.06 (d, J = 5) | 5.63 (dd, J = 5,8) | 5.34 (d, J = 14)<br>5.56 (d, J = 14) | 3.91 (s) | 9.23 (d, J = 8) | 7.47 (m)<br>7.24 (dd, J = 2,8) | 9.30 (s)<br>8.51 (d, J = 8)<br>8.13 (m) | 8.63 (m)<br>8.16 (m)<br>3.78 (s)<br>3.35 (m)<br>2.92 (m) |
| 44 | 3.51 (d, J = 18)<br>3.07 (d, J = 18) | 5.03 (d, J = 5) | 5.58 (dd, J = 5,8) | 5.15 (d, J = 13)<br>5.57 (d, J = 13) | 3.87 (s) | 9.29 (d, J = 8) | 7.44 (m)<br>7.21 (dd, J = 2,8) | 8.00 (d, J = 6)<br>9.18 (d, J = 6) | 8.10 (br s)<br>4.63 (d, J = 5)<br>3.73 (s) |
| 45 | 3.50 (d, J = 18)<br>3.13 (d, J = 18) | 5.02 (d, J = 5) | 5.61 (dd, J = 5,7) | 5.71 (d, J = 14)<br>5.28 (d, J = 14) | 3.87 (s) | 9.20 (d, J = 8) | 7.42–7.45 (m)<br>7.21 (dd, J = 2,8) | 9.63 (s)<br>8.97–9.03 (m)<br>8.50–8.58 (m)<br>8.08 (dd, J = 6,8) | 9.20 (d, J = 8)<br>7.92 (br s)<br>4.15 (br s)<br>2.50–3.19 (m) |

TABLE II

MS DATA

| Cmpd. of Example | R¹ | Ar | Isolated Form | MS |
|---|---|---|---|---|
| 1 | m-CONH$_2$ | 2,4,5-triClPh | zwitterion | M+ = 586 |
| 2 | m-NHCOCH$_2$NH$_2$ | 2,4,5-triClPh | CF$_3$CO$_2$H salt | MH+ = 616 |
| 3 | m-CONH$_2$ | 2,5-diClPh | HCl salt | MH+ = 553 |
| 4 | m-CONH$_2$ | 3-BrPh | zwitterion | MH+ = 563 |
| 5 | m-CONH$_2$ | 2,5-diMe,4-ClPh | zwitterion | MH+ = 547 |
| 6 | m-CONHCH$_3$ | 2,4,5-triClPh | zwitterion | MH+ = 601 |
| 7 | m-CONHCH$_2$OH | 2,5-diClPh | zwitterion | MH+ = 583 |
| 8 | m-CONHCH$_2$OH | 2,4,5-triClPh | HI salt | MH+ = 617 |
| 9 | m-CONHCH$_2$CH$_2$NH$_2$ | 2,5-diClPh | HCl salt | MH+ = 596 |
| 10 | m-CONHCH$_2$CH$_2$NH$_2$ | 2,4,5-triClPh | CF$_3$CO$_2$H salt | MH+ = 630 |
| 11 | m-CONHCH$_2$CH$_2$NH$_2$ | 3-BrPh | CF$_3$CO$_2$H salt | MH+ = 606 |
| 12 | m-CONHCH$_2$CH$_2$NH$_2$ | 2-Cl,5-CF$_3$Ph | mixed HI/CF$_3$CO$_2$H salt | MH+ = 630 |
| 13 | m-CONHCH$_2$CH$_2$NH$_2$ | 1-naphthyl | CF$_3$CO$_2$H salt | MH+ = 578 |
| 14 | m-CONHCH$_2$CH$_2$NH$_2$ | 2-benzthiazolyl | CF$_3$CO$_2$H salt | MH+ = 585 |
| 15 | m-CONH(CH$_2$)$_3$NH$_2$ | 2,5-diClPh | CF$_3$CO$_2$H salt | MH+ = 609 |
| 16 | m-COCH$_3$ | 2,4,5-triClPh | HCl salt | MH+ = 586 |
| 17 | m-CN | 2,4,5-triClPh | HCl salt | MH+ = 569 |
| 18 | m-CH$_2$NH$_2$ | 2,5-diClPh | CF$_3$CO$_2$H salt | MH+ = 539 |
| 19 | m-CH$_2$NH$_2$ | 2,4,5-triClPh | CF$_3$CO$_2$H salt | MH+ = 573 |
| 20 | m-CH$_2$NH$_2$ | 2-Cl,5-CF$_3$Ph | CF$_3$CO$_2$H salt | MH+ = 573 |
| 21 | m-CH$_2$OH | 2,5-diClPh | zwitterion | MH+ = 540 |
| 22 | m-CH$_2$OH | 2,4,5-triClPh | zwitterion | MH+ = 574 |
| 23 | m-CH$_2$CONH$_2$ | 2,5-diClPh | zwitterion | MH+ = 567 |
| 24 | m-NHCONH$_2$ | 2,5-diClPh | zwitterion | MH+ = 568 |
| 25 | m-NHCONH$_2$ | 2,4,5-triClPh | zwitterion | MH+ = 602 |
| 26 | m-NHCOCH$_2$NH$_2$ | 2,5-diClPh | CF$_3$CO$_2$H salt | MH+ = 582 |
| 27 | m-NHCO(CH$_2$)$_2$NH$_2$ | 2,5-diClPh | CF$_3$CO$_2$H salt | MH+ = 595 |
| 28 | p-CONH$_2$ | 2,5-diClPh | HI salt | MH+ = 553 |
| 29 | p-CONH$_2$ | 2,4,5-triClPh | HI salt | MH+ = 587 |
| 30 | p-CONHCH$_2$CH$_2$NH$_2$ | 2,5-diClPh | CF$_3$CO$_2$H salt | MH+ = 596 |
| 31 | p-CONHCH$_2$CH$_2$NH$_2$ | 2,4,5-triClPh | CF$_3$CO$_2$H salt | MH+ = 630 |
| 32 | p-CH$_2$NH$_2$ | 2,5-diClPh | HCl salt | MH+ = 539 |
| 33 | p-CH$_2$OH | 2,5-diClPh | zwitterion | MH+ = 540 |
| 34 | o-CH$_2$NH$_2$ | 2,4,5-triClPh | CF$_3$CO$_2$H salt | MH+ = 573 |
| 35 | o-CH$_2$OH | 2,5-diClPh | zwitterion | MH+ = 540 |
| 36 | o-CH$_2$CH$_2$NH$_2$ | 2,4,5-triClPh | CF$_3$CO$_2$H salt | MH+ = 586 |
| 37 | o-CH$_2$CH$_2$OH | 2,5-diClPh | zwitterion | MH+ = 554 |
| 38 | m-CONHCH$_2$CH(OH)CH$_2$NH$_2$ | 2,5-diClPh | CF$_3$CO$_2$H salt | MH+ = 622 |
| 39 | 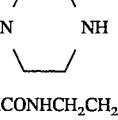 m-CON-piperazine-NH | 2,5-diClPh | CF$_3$CO$_2$H salt | MH+ = 626 |
| 40 | m-NHCONHCH$_2$CH$_2$NH$_2$ | 2,5-diClPh | CF$_3$CO$_2$H salt | MH+ = 611 |
| 41 | 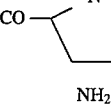 m-NHCO-(pyrrolidinyl-NH) | 2,5-diClPh | CF$_3$CO$_2$H salt | MH+ = 622 |
| 42 | 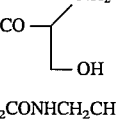 m-NHCO-CH(NH$_2$)-CH$_2$OH | 2,5-diClPh | CF$_3$CO$_2$H salt | MH+ = 612 |
| 43 | m-CH$_2$CONHCH$_2$CH$_2$NH$_2$ | 2,5-diClPh | CF$_3$CO$_2$H salt | MH+ = 610 |
| 44 | p-CH$_2$NHCOCH$_2$NH$_2$ | 2,5-diClPh | CF$_3$CO$_2$H salt | MH+ = 596 |
| 45 | m-NHC(O)CH$_2$CH(OH)CH$_2$NH$_2$ | 2,5-diClPh | CF$_3$CO$_2$H salt | MH+ = 626 |

We claim:

1. A compound having the formula

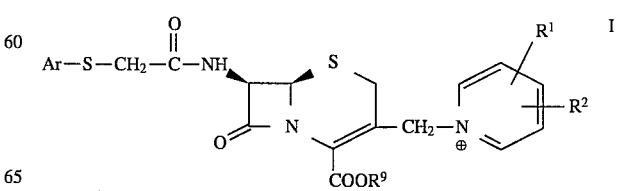

wherein Ar is an aryl group selected from the group consisting of

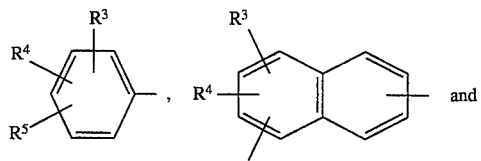

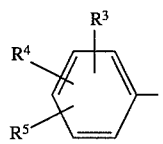

in which $R^3$, $R^4$ and $R^5$ are each independently hydrogen, halogen, trihalomethyl, nitro, $C_1$–$C_6$ alkyl, —$(CH_2)_nOR^6$ or —$(CH_2)_nSR^6$, with the proviso that when Ar is a phenyl group, $R^3$, $R^4$ and $R^5$ may not all be hydrogen; n is an integer of from 1 to 6; $R^6$ is hydrogen or $C_1$–$C_6$ alkyl; $R^1$ and $R^2$ are each independently hydrogen, —$(CH_2)_m CONR^7R^8$, —$(CH_2)_mCOR^7$, —$(CH_2)_mCO_2 R^7$, —$(CH_2)_mCN$, —$(CH_2)_mNR^7 R^8$, —$(CH_2)_mOR^7$, —$(CH_2)_mNHCONR^7R^8$ or —$(CH_2)_m NHCOR^7$ in which m is 0 or an integer of from 1 to 6 and $R^7$ and $R^8$ are each independently hydrogen, $C_1$–$C_6$ alkyl substituted by one or two amino or hydroxyl groups, or a group of the formula

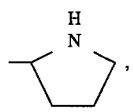

or $R^7$ and $R^8$ taken together with the nitrogen atom to which they are attached represent

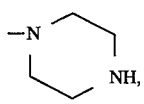

with the proviso that $R^1$ and $R^2$ may not both be hydrogen; and $R^9$ is hydrogen, an anionic charge or a carboxyl-protecting group, provided that when $R^9$ is hydrogen or a protecting group, there is also present a counter ion; or a pharmaceutically acceptable salt thereof.

2. A compound according to claim 1 wherein Ar is

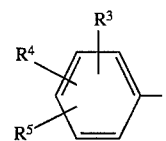

in which $R^3$, $R^4$, and $R^5$ are each independently hydrogen, halogen, trihalomethyl, $C_1$–$C_6$ alkyl, —$(CH_2)_n OR^6$ or —$(CH_2)_nSR^6$, with the proviso that $R^3$, $R^4$ and $R^5$ may not all be hydrogen; n is an integer of from 1 to 6; and $R^6$ is hydrogen or $C_1$–$C_6$ alkyl.

3. A compound according to claim 2 wherein Ar is

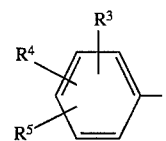

in which $R^3$, $R^4$ and $R^5$ are each independently hydrogen, halogen, trihalomethyl or $C_1$–$C_6$ alkyl.

4. A compound according to claim 3 wherein $R^1$ is hydrogen and $R^2$ is —$(CH_2)_mCONR^7R^8$, —$(CH_2)_mCOR^7$, —$(CH_2)_mCN$, —$(CH_2)_m NR^7R^8$, —$(CH_2)_mOR^7$, —$(CH^2)_mNHCONR^7R^8$ or —$(CH_2)_mNHCOR^7$ in which m is 0 or an integer of from 1 to 6 and $R^7$ and $R^8$ are each independently hydrogen, $C_1$–$C_6$ alkyl substituted by one or two amino or hydroxyl groups or a group of the formula

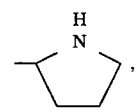

or $R^7$ and $R^8$ taken together with the nitrogen atom to which they are attached represent

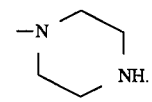

5. A compound according to claim 4 wherein Ar is

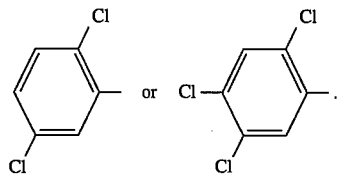

6. A compound having the formula

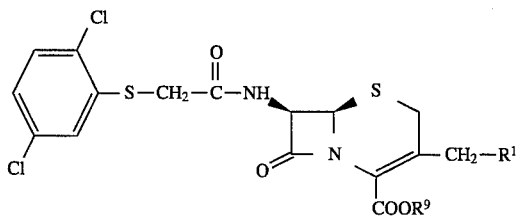

(a)

wherein $R^{10}$ is

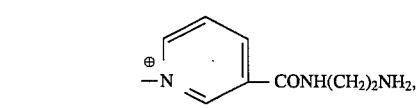

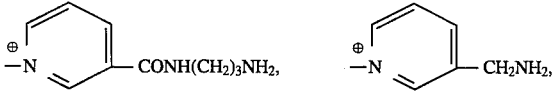

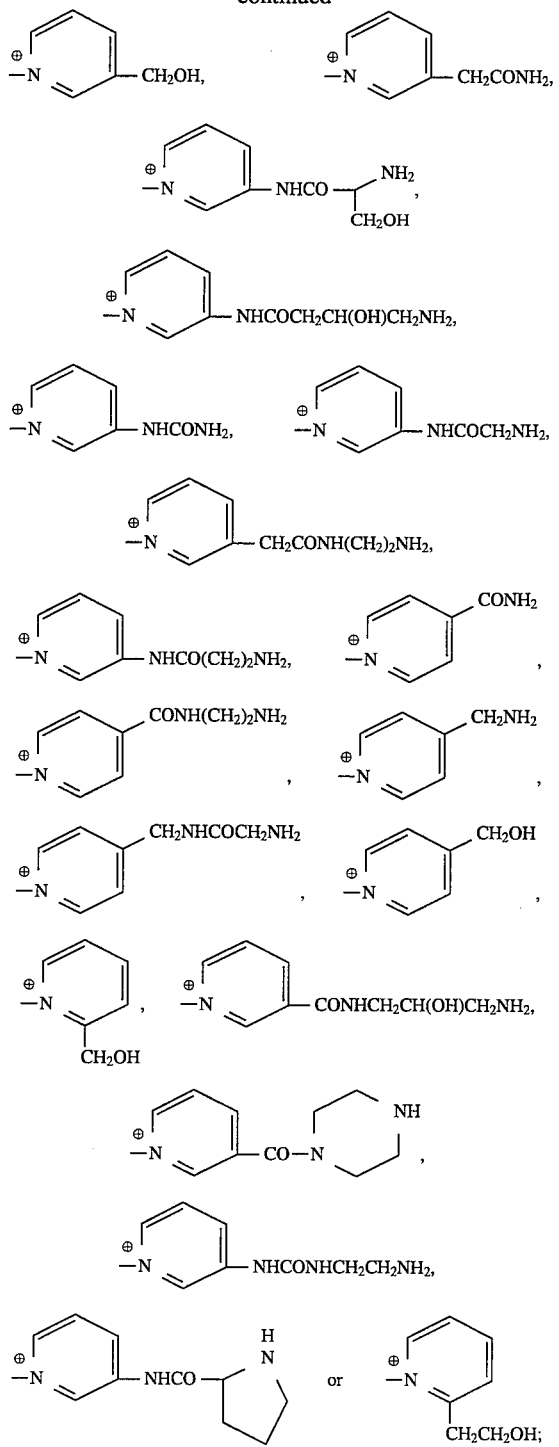
and $R^9$ is hydrogen, an anionic charge or a carboxyl-protecting group, provided that when $R^9$ is hydrogen or a protecting group, there is also present a counter ion;
wherein $R^{10}$ is
and $R^9$ is as defined above;

wherein $R^{10}$ is

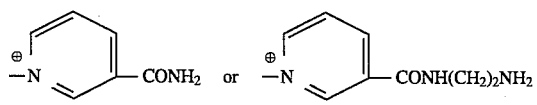

and $R^9$ is as defined above;

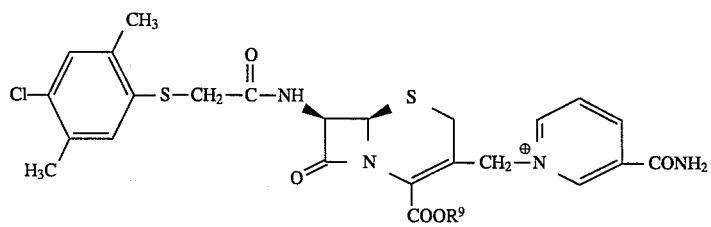

wherein $R^9$ is as defined above;

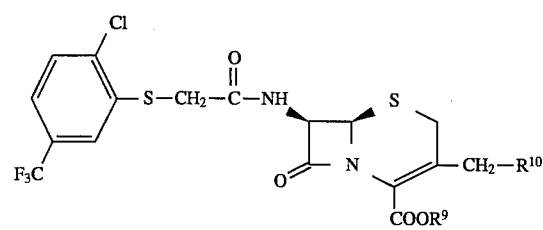

wherein $R^{10}$ is

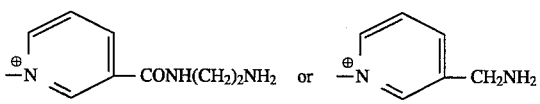

and $R^9$ is as defined above;

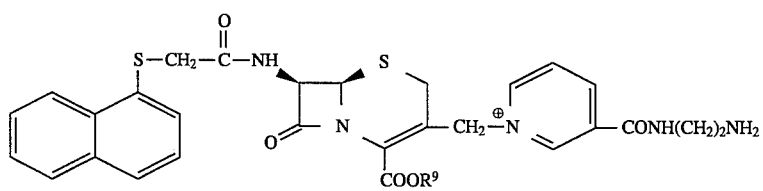

and $R^9$ is as defined above; or

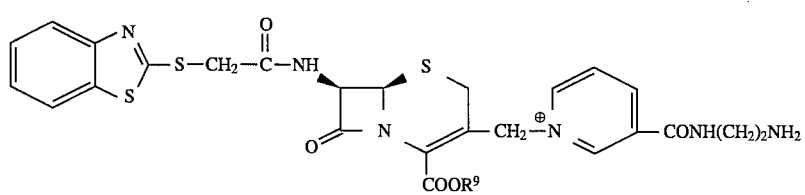

and $R^9$ is as defined above; or a pharmaceutically acceptable salt thereof.

7. A compound selected from the group consisting of

1-[[(6R)-trans-2-Carboxy-8-oxo- 7-[2-(2,5-dichlorophenylthio)acetamido]- 5-thia-1-azabicyclo[4.2.0]-oct-2-en- 3-yl]methyl]-3-(aminocarbonyl)pyridinium inner salt;

1-[[(6R)-trans-2-Carboxy-8-oxo- 7-[2-(2,4,5-trichlorophenylthio)acetamido]- 5-thia-1-azabicyclo[4.2.0]-oct-2-en- 3-yl]methyl]-3-(aminocarbonyl)pyridinium inner salt;

1-[[(6R)-trans-2-Carboxy-8-oxo- 7-[2-(3-bromophenylthio)acetamido]-5-thia- 1-azabicyclo[4.2.0]-oct-2-en-3-yl]methyl]-3-(aminocarbonyl)pyridinium inner salt;

1-[[(6R)-trans-2-Carboxy-8-oxo- 7-[2-(2,5-dimethyl-4-chlorophenylthio) acetamido]-5-thia-1-azabicyclo [4.2.0]-oct- 2-en-3-yl]methyl]-3-(aminocarbonyl)pyridinium inner salt;

1-[[(6R)-trans-2-Carboxy-8-oxo- 7-[2-(2,4,5-trichlorophenylthio)acetamido]-5 -thia-1-azabicyclo[4.2.0]-oct-2-en-3-yl]methyl]-3-(methylaminocarbonyl)pyridinium inner salt;

1-[[(6R)-trans-2-Carboxy-8-oxo-7 -[2-(2,5-dichlorophenylthio)acetamido]-5-thia- 1-azabicyclo[4.2.0]-oct-2-en-3-yl]methyl]-3-[(hydroxymethyl)aminocarbonyl]-pyridinium inner salt;

1-[[(6R)-trans-2-Carboxy-8-oxo-7 -[2-(2,4,5-trichlorophenylthio)acetamido]-5 -thia-1-azabicyclo[4.2.0]-oct-2-en-3-yl]methyl]-3-[(hydroxymethyl)aminocarbonyl]-pyridinium inner salt;

1-[[(6R)-trans-2-Carboxy-8-oxo-7 -[2-(2,5-dichlorophenylthio)acetamido]-5-thia- 1-azabicyclo[4.2.0]-oct-2-en-3-yl]methyl]-3-[(2-aminoethyl)aminocarbonyl]-pyridinium inner salt;

1-[[(6R)-trans-2-Carboxy-8-oxo-7 -[2-(2,4,5-trichlorophenylthio)acetamido]-5 -thia-1-azabicyclo[4.2.0]-oct-2-en-3-yl]methyl]-3-[(2-aminoethyl)aminocarbonyl]-pyridinium inner salt;

1-[[(6R)-trans-2-Carboxy-8-oxo-7 -[2-(3-bromophenylthio)acetamido]-5-thia-1 -azabicyclo[4.2.0]-oct-2-en-3-yl]methyl]- 3-[(2-aminoethyl)aminocarbonyl]-pyridinium inner salt;

1-[[(6R)-trans-2-Carboxy-8-oxo-7 -[2-(2-chloro-5-trifluoromethylphenylthio) -acetamido]-5-thia-1-azabicyclo[4.2.0]-oct- 2-en-3-yl]methyl]-3-[(2-amino -ethyl)aminocarbonyl]pyridinium inner salt;

1-[[(6R)-trans-2-Carboxy-8-oxo-7 -[2-(1-naphthylthio) acetamido]-5-thia-1 -azabicyclo[4.2.0]-oct-2-en-3-yl] methyl]- 3-[(2-aminoethyl)aminocarbonyl]pyridinium inner salt;

1-[[(6R)-trans-2-Carboxy-8-oxo-7 -[2-(2-benzthiazolylthio)acetamido]-5-thia- 1-azabicyclo[4.2.0]-oct-2-en-3-yl]methyl]-3-[(2-aminoethyl)aminocarbonyl]pyridinium inner salt;

1-[[(6R)-trans-2-Carboxy-8-oxo-7 -[2-(2,5-dichlorophenylthio)acetamido]-5-thia- 1-azabicyclo[4.2.0]-oct-2-en-3-yl]methyl]-3-[(3-aminopropyl)aminocarbonyl]-pyridinium inner salt;

1-[[(6R)-trans-2-Carboxy-8-oxo-7 -[2-(2,4,5-trichlorophenylthio)acetamido]-5 -thia-1-azabicyclo[4.2.0]-oct-2-en-3-yl]methyl]-3-(acetyl)pyridinium inner salt;

1-[[(6R)-trans-2-Carboxy-8-oxo- 7-[2-(2,4,5-trichlorophenylthio)acetamido]-5 -thia-1-azabicyclo[4.2.0]-oct-2-en-3-yl]methyl]-3-(cyano)pyridinium inner salt;

1-[[(6R)-trans-2-Carboxy-8-oxo-7 -[2-(2,5-dichlorophenylthio)acetamido]-5-thia- 1-azabicyclo[4.2.0]-oct-2-en-3-yl]methyl]-3-(aminomethyl)pyridinium inner salt;

1-[[(6R)-trans-2-Carboxy-8-oxo-7 -[2-(2,4,5-trichlorophenylthio)acetamido]-5 -thia-1-azabicyclo[4.2.0]-oct-2-en-3-yl]methyl]-3-(aminomethyl)pyridinium inner salt;

1-[[(6R)-trans-2-Carboxy-8-oxo-7 -[2-(2-chloro-5-trifluoromethylphenylthio) -acetamido]-5-thia-1-azabicyclo[4.2.0]-oct- 2-en-3-yl]methyl]-3-(aminomethyl)-pyridinium inner salt;

1-[[(6R)-trans-2-Carboxy-8-oxo-7 -[2-(2,5-dichlorophenylthio)acetamido]-5-thia- 1-azabicyclo[4.2.0]-oct-2-en-3-yl]methyl]-3-(hydroxymethyl)pyridinium inner salt;

1-[[(6R)-trans-2-Carboxy-8-oxo-7 -[2-(2,4,5-trichlorophenylthio)acetamido]-5-thia -1-azabicyclo[4.2.0]-oct-2-en-3-yl]methyl]-3-(hydroxymethyl)pyridinium inner salt;

1-[[(6R)-trans-2-Carboxy-8-oxo-7 -[2-(2,5-dichlorophenylthio)acetamido]-5-thia- 1-azabicyclo[4.2.0]-oct-2-en-3-yl]methyl]-3-(carbamylmethyl)pyridinium inner salt;

1-[[(6R)-trans-2-Carboxy-8-oxo-7 -[2-(2,5-dichlorophenylthio)acetamido]-5-thia- 1-azabicyclo[4.2.0]-oct-2-en-3-yl]methyl]-3-(ureido)pyridinium inner salt;

1-[[(6R)-trans-2-Carboxy-8-oxo-7 -[2-(2,4,5-trichlorophenylthio)acetamido]-5-thia -1-azabicyclo[4.2.0]-oct-2-en-3-yl]methyl]-3-(ureido)pyridinium inner salt;

1-[[(6R)-trans-2-Carboxy-8-oxo-7 -[2-(2,5-dichlorophenylthio)acetamido]-5-thia- 1-azabicyclo[4.2.0]-oct-2-en-3-yl]methyl]-3-(aminomethylcarbonylamino)-pyridinium inner salt;

1-[[(6R)-trans-2-Carboxy-8-oxo-7 -[2-(2,4,5-trichlorophenylthio)acetamido]-5-thia -1-azabicyclo[4.2.0]-oct-2-en-3-yl]methyl]-3-(aminomethylcarbonylamino)-pyridinium inner salt;

1-[[(6R)-trans-2-Carboxy-8-oxo-7 -[2-(2,5-dichlorophenylthio)acetamido]-5-thia- 1-azabicyclo[4.2.0]-oct-2-en-3-yl]methyl]-3-[(2-aminoethyl)carbonylamino]-pyridinium inner salt;

1-[[(6R)-trans-2-Carboxy-8-oxo-7 -[2-(2,5-dichlorophenylthio)acetamido]-5-thia- 1-azabicyclo[4.2.0]-oct-2-en-3-yl]methyl]-4-(aminocarbonyl)pyridinium inner salt;

1-[[(6R)-trans-2-Carboxy-8-oxo-7 -[2-(2,4,5-trichlorophenylthio)acetamido]-5-thia -1-azabicyclo[4.2.0]-oct-2-en-3-yl]methyl]-4-(aminocarbonyl)pyridinium inner salt;

1-[[(6R)-trans-2-Carboxy-8-oxo-7 -[2-(2,5-dichlorophenylthio)acetamido]-5-thia- 1-azabicyclo[4.2.0]-oct-2-en-3-yl]methyl]-4-[(2-aminoethyl)aminocarbonyl]-pyridinium inner salt;

1-[[(6R)-trans-2-Carboxy-8-oxo-7 -[2-(2,4,5-trichlorophenylthio)acetamido]-5-thia -1-azabicyclo[4.2.0]-oct-2-en-3-yl]methyl]-4-[(2-aminoethyl)aminocarbonyl]-pyridinium inner salt;

1-[[(6R)-trans-2-Carboxy-8-oxo-7 -[2-(2,5-dichlorophenylthio)acetamido]-5-thia- 1-azabicyclo[4.2.0]-oct-2-en-3-yl]methyl]-4-(aminomethyl)pyridinium inner salt;

1-[[(6R)-trans-2-Carboxy-8-oxo-7 -[2-(2,5-dichlorophenylthio)acetamido]-5-thia- 1-azabicyclo[4.2.0]-oct-2-en-3-yl]methyl]-4-(hydroxymethyl)pyridinium inner salt;

1-[[(6R)-trans-2-Carboxy-8-oxo-7 -[2-(2,4,5-trichlorophenylthio)acetamido]-5-thia -1-azabicyclo[4.2.0]-oct-2-en-3-yl]methyl]-2-(aminomethyl)pyridinium inner salt;

1-[[(6R)-trans-2-Carboxy-8-oxo-7 -[2-(2,5-dichlorophenylthio)acetamido]-5-thia- 1-azabicyclo[4.2.0]-oct-2-en-3-yl]methyl]-2-(hydroxymethyl)pyridinium inner salt;

1-[[(6R)-trans-2-Carboxy-8-oxo-7 -[2-(2,4,5-trichlorophenylthio)acetamido]-5-thia -1-azabicyclo[4.2.0]-oct-2-en-3-yl]methyl]-2-(2-aminoethyl)pyridinium inner salt;

1-[[(6R)-trans-2-Carboxy-8-oxo-7 -[2-(2,5-dichlorophenylthio)acetamido]-5-thia- 1-azabicyclo[4.2.0]-oct-2-en-3-yl]methyl]-2-(2-hydroxyethyl)pyridinium inner salt;

1-[[(6R)-trans-2-Carboxy-8-oxo-7 -[2-(2,5-dichlorophenylthio)acetamido]-5-thia- 1-azabicyclo[4.2.0]-oct-2-en-3-yl]methyl]-3-[(3-amino-2-hydroxypropyl)aminocarbonyl]pyridinium inner salt;

1-[[(6R)-trans-2-Carboxy-8-oxo-7 -[2-(2,5-dichlorophenylthio)acetamido]-5-thia- 1-azabicyclo[4.2.0]-oct-2-en-3-yl]methyl]-3-(piperizino-N-carbonyl)-pyridinium inner salt;

1-[[(6R)-trans-2-Carboxy-8-oxo-7 -[2-(2,5-dichlorophenylthio)acetamido]-5-thia- 1-azabicyclo[4.2.0]-oct-2-en-3-yl]methyl]-3-[(2-aminoethyl)ureido]pyridinium inner salt;

1-[[(6R)-trans-2-Carboxy-8-oxo-7 -[2-(2,5-dichlorophenylthio)acetamido]-5-thia- 1-azabicyclo[4.2.0]-oct-2-en-3-yl]methyl]-3-[(2-pyrrolidinyl)carbonylamino]-pyridinium inner salt;

1-[[(6R)-trans-2-Carboxy-8-oxo-7 -[2-(2,5-dichlorophenylthio)acetamido]-5-thia- 1-azabicyclo[4.2.0]-oct-2-en-3-yl]methyl]-3-[(1-(1-amino-2-hydroxy)ethyl)carbonyl -amino)pyridinium inner salt;

1-[[(6R)-trans-2-Carboxy-8-oxo-7 -[2-(2,5-dichlorophenylthio)acetamido]-5-thia- 1-azabicyclo[4.2.0]-oct-2-en-3-yl]methyl]-3-[(2-aminoethyl)carbamylmethyl]-pyridinium inner salt;

1-[[(6R)-trans-2-Carboxy-8-oxo-7 -[2-(2,5-dichlorophenylthio)acetamido]-5-thia- 1-azabicyclo[4.2.0]-oct-2-en-3-yl]methyl]-4-[(aminomethylcarbonyl)amino-methyl]pyridinium inner salt; and 1-[[(6R)-trans-2-Carboxy-8-oxo-7 -[2-(2,5-dichlorophenylthio)acetamido]-5-thia- 1-azabicyclo[4.2.0]-oct-2-en-3-yl]methyl]-3-[(3-amino-2-hydroxypropyl)carbonylamino]pyridinium inner salt;

or a pharmaceutically acceptable salt thereof.

8. A compound selected from the group consisting of

1-[[(6R)-trans-2-Carboxy-8-oxo-7 -[2-(2,5-dichlorophenylthio)acetamido]-5-thia- 1-azabicyclo[4.2.0]-oct-2-en-3-yl]methyl]-3-[(2-aminoethyl)aminocarbonyl]-pyridinium inner salt;

1-[[(6R)-trans-2-Carboxy-8-oxo-7 -[2-(2,4,5-trichlorophenylthio)-acetamido]-5-thia -1-azabicyclo[4.2.0]-oct-2-en-3-yl]methyl]-3-[(2-aminoethyl)aminocarbonyl]-pyridinium inner salt;

1-[[(6R)-trans-2-Carboxy-8-oxo-7 -[2-(3-bromophenylthio)acetamido]-5-thia-1 -azabicyclo[4.2.0]-oct-2-en-3-yl]methyl]- 3-[(2-aminoethyl)aminocarbonyl]pyridinium inner salt;

1-[[(6R)-trans-2-Carboxy-8-oxo-7 -[2-(2-chloro-5-trifluoromethylphenylthio) -acetamido]-5-thia-1-azabicyclo[4.2.0]-oct- 2-en-3-yl]methyl]-3-[(2-aminoethyl)aminocarbonyl]pyridinium inner salt;

1-[[(6R)-trans-2-Carboxy-8-oxo-7 -[2-(2,5-dichlorophenylthio)acetamido]-5-thia- 1-azabicyclo[4.2.0]-oct-2-en-3-yl]methyl]-3-[(3-aminopropyl)aminocarbonyl]-pyridinium inner salt;

1-[[(6R)-trans-2-Carboxy-8-oxo-7 -[2-(2,5-dichlorophenylthio)acetamido]-5-thia- 1-azabicyclo[4.2.0]-oct-2-en-3-yl]methyl]-3-(aminomethylcarbonylamino)-pyridinium inner salt;

1-[[(6R)-trans-2-Carboxy-8-oxo-7 -[2-(2,4,5-trichlorophenylthio)-acetamido]-5-thia -1-azabicyclo[4.2.0]-oct-2-en-3-yl]methyl]-3-(aminomethylcarbonylamino)-pyridinium inner salt;

1-[[(6R)-trans-2-Carboxy-8-oxo-7 -[2-(2,5-dichlorophenylthio)acetamido]-5-thia- 1-azabicyclo[4.2.0]-oct-2-en-3-yl]methyl]-3-[(2-aminoethyl)carbonylamino)-pyridinium inner salt;

1-[[(6R)-trans-2-Carboxy-8-oxo-7 -[2-(2,5-dichlorophenylthio)acetamido]-5-thia- 1-azabicyclo[4.2.0]-oct-2-en-3-yl]methyl]-4-[(2-aminoethyl)aminocarbonyl]-pyridinium inner salt;

1-[[(6R)-trans-2-Carboxy-8-oxo-7 -[2-(2,4,5-trichlorophenylthio)-acetamido]-5-thia -1-azabicyclo[4.2.0]-oct-2-en-3-yl]methyl]-4-[(2-aminoethyl)aminocarbonyl]-pyridinium inner salt; and 1-[[(6R)-trans-2-Carboxy-8-oxo-7 -[2-(2,5-dichlorophenylthio)acetamido]-5-thia- 1-azabicyclo[4.2.0]-oct-2-en-3-yl]methyl]-3-[(3-amino-2-hydroxypropyl)carbonylamino]pyridinium inner salt;

or a pharmaceutically acceptable salt thereof.

9. A compound of the formula

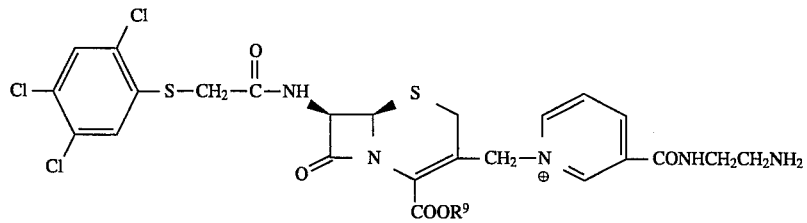

wherein $R^9$ is hydrogen, an anionic charge or a carboxyl-protecting group, provided that when $R^9$ is hydrogen or a protecting group, there is also present a counter ion; or a pharmaceutically acceptable salt thereof.

10. A compound of the formula

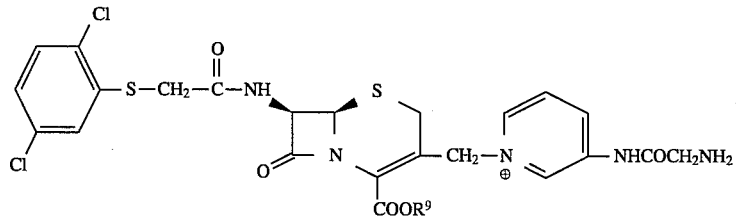

wherein $R^9$ is hydrogen, an anionic charge or a carboxyl-protecting group, provided that when $R^9$ is hydrogen or a protecting group, there is also present a counter ion; or a pharmaceutically acceptable salt thereof.

11. A pharmaceutical composition comprising an effective antibacterial amount of a compound of claim 1 and a pharmaceutically acceptable carrier or diluent.

12. A method of treating a bacterial infection which comprises administering to a host afflicted with such infection an effective antibacterial amount of a compound of claim 1.

13. A method of treating a bacterial infection caused by a strain of methicillin-resistant *Staphylococcus aureus* which comprises administering to a host afflicted with such infection an effective antibacterial amount of a compound of claim 1.

* * * * *